US011040161B1

(12) United States Patent
Bui

(10) Patent No.: US 11,040,161 B1
(45) Date of Patent: Jun. 22, 2021

(54) GASTRO-INTESTINAL (G.I.) ENDOSCOPY MASK AND METHODS OF MAKING AND USING SAME

(71) Applicant: Phong Duy Bui, San Diego, CA (US)

(72) Inventor: Phong Duy Bui, San Diego, CA (US)

( * ) Notice: Subject to any disclaimer, the term of this patent is extended or adjusted under 35 U.S.C. 154(b) by 0 days.

(21) Appl. No.: 17/105,937

(22) Filed: Nov. 27, 2020

(51) Int. Cl.
*A61M 16/04* (2006.01)
*A61M 16/06* (2006.01)
*A61M 16/10* (2006.01)
*A61B 1/00* (2006.01)

(52) U.S. Cl.
CPC ..... *A61M 16/0463* (2013.01); *A61B 1/00135* (2013.01); *A61B 1/00137* (2013.01); *A61B 1/00142* (2013.01); *A61M 16/0493* (2014.02); *A61M 16/0622* (2014.02); *A61M 16/0688* (2014.02); *A61M 16/1005* (2014.02); *A61M 2016/103* (2013.01); *A61M 2016/1025* (2013.01)

(58) Field of Classification Search
CPC .......... A61M 16/0415; A61M 16/0463; A61M 16/0493; A61M 16/0497; A61M 16/06–16/0655; A61M 16/0688; A61B 1/00135; A61B 1/00137; A61B 1/00142; A61B 1/24; A61B 1/267–2676; A61B 1/273–2736
See application file for complete search history.

(56) References Cited

U.S. PATENT DOCUMENTS

| 4,848,331 A * | 7/1989 | Northway-Meyer ....................... A61M 16/0495 128/200.26 |
| 5,386,817 A * | 2/1995 | Jones ................. A61B 1/00091 138/108 |
| 6,196,223 B1 * | 3/2001 | Belfer ................ A41D 13/1176 128/205.25 |
| 8,365,734 B1 * | 2/2013 | Lehman ................ A61M 16/12 128/206.28 |
| 8,739,795 B2 | 6/2014 | Kanowitz |
| 10,040,231 B2 | 8/2018 | Nasir |
| 10,493,228 B2 | 12/2019 | Reddy et al. |
| 10,709,858 B2 | 7/2020 | McDonald |
| 2008/0053449 A1 * | 3/2008 | Lindblom .......... A61B 1/00154 128/206.21 |

(Continued)

OTHER PUBLICATIONS

"AIR Tent for Airway Management of SARS Patients", Canadian Journal of Anesthesiza, p. 854, 2003.

*Primary Examiner* — Valerie L Woodward
(74) *Attorney, Agent, or Firm* — James R. McDaniel

(57) ABSTRACT

The improved endoscopy mask is a single-use, lightweight, disposable, easy-to-use endoscopy mask that is secured around the patient's head and neck. It contains the spread of any respiratory pathogens during upper G.I. endoscopy and extubation, thereby allowing the gastroenterologist to insert and withdraw the gastroscope (upper G.I. endoscope) through an opening in the mask. The mask can be utilized for airway intervention to contain pathogens in the intensive care unit (ICU), emergency department (ED), operating room (OR), and the G.I. endoscopy suite. It can also potentially be utilized away from the hospital in ambulances, hospice care, and nursing homes. The endoscopy mask confines potentially dangerous airway secretions to a sealed area around the patient's nose and mouth.

17 Claims, 19 Drawing Sheets

(56) References Cited

U.S. PATENT DOCUMENTS

| | | | |
|---|---|---|---|
| 2012/0285448 A1* | 11/2012 | Dugan | A61M 16/0694 |
| | | | 128/202.16 |
| 2013/0023729 A1* | 1/2013 | Vazales | A61M 16/0463 |
| | | | 600/104 |
| 2013/0296653 A1* | 11/2013 | Brown | A61B 1/00154 |
| | | | 600/114 |
| 2016/0082211 A1 | 3/2016 | Chedid et al. | |
| 2019/0091434 A1* | 3/2019 | Reddy | A61M 16/14 |

* cited by examiner

GASTRO-INTESTINAL (G.I.) ENDOSCOPY MASK AND METHODS OF MAKING AND USING SAME

FIELD OF THE INVENTION

The present invention is generally related to an improved Gastro-Intestinal (G.I.) endoscopy mask. The improved G.I. endoscopy mask is a novel, single-use, lightweight, disposable, easy-to-use endoscopy mask that is secured around the patient's head and neck. It contains the spread of any respiratory pathogens during an upper G.I. endoscopy procedure thereby allowing the gastroenterologist (doctor) to insert and withdraw the gastroscope (upper G.I. endoscope) through an opening in the mask. The mask can also be used for extubation thereby allowing the anesthesiologist to place the mask over the endo-tracheal tube ("ET tube") through an opening in the mask. The mask can be utilized for airway intervention to contain pathogens in the intensive care unit (ICU), emergency department (ED), operating room (OR), and the G.I. endoscopy suite. It can also potentially be utilized away from the hospital in ambulances, hospice care, and nursing homes. The endoscopy mask confines potentially dangerous airway secretions to a sealed area around the patient's nose and mouth. The mask may decrease the use of medical/surgical supplies which can be provided to other high-risk areas, decrease the cost of overall personal protective equipment (PPE), and provide lifesaving protection for healthcare workers involved in high risk pathogen aerosolizing procedures.

BACKGROUND OF THE INVENTION

Prior to the present invention, as set forth in general terms above and more specifically below, it is known, that the SARS-CoV-2 virus is transmitted primarily by person-to-person contact through respiratory droplets and aerosols. This virus causes coronavirus disease 2019 (COVID-19), which may clinically present with flu-like symptoms (fever, cough, fatigue) and progress to acute respiratory failure (shortness of breath, pneumonia, acute respiratory distress).

Medical personnel caring for patients with respiratory failure from COVID-19 are at high risk of contracting the infection. Procedures generating aerosols such as upper G.I. endoscopy and E.T. (endo-tracheal) tube extubation in addition to others are of particularly high risk.

Appropriate precautions are vital when performing these procedures in the operating room (OR), G.I. endoscopy suite, emergency department (ED), and intensive care unit (ICU). Unfortunately, many hospitals lack personal protective equipment (PPE) of sufficiently high quality (n95 masks, powered air purifying respirators (PAPR), and negative pressure isolation) for urgent yet dangerous aerosol-generating procedures such as upper G.I. endoscopy and an E.T. tube extubation from a patient.

With the COVID-19 pandemic, frequent life-saving upper airway intervention is critical yet very risky to the healthcare provider and staff. Over half of COVID-19 patients are afebrile early in the disease, but can still spread SARS-CoV-2 with high efficiency. The virus is present in its highest concentrations in the upper airway (nose and mouth), thereby placing those health care workers in primary and critical care, anesthesiology, otolaryngology, and dentistry at greatest risk. The latest figures reveal healthcare workers make up 9% of Italy's COVID-19 cases and 12% of cases in Spain. Not adequately protecting healthcare workers during an epidemic will cripple the healthcare system and exponentially increase patient morbidity and mortality. Healthcare workers are becoming infected at unprecedented rates. In fact, some hospital systems are now using a trash bag with a hole in it to attempt to minimize aerosolization during intubation.

Furthermore, prior to the present invention, as set forth in general terms above and more specifically below, it is known, to employ various types of patient masks. See for example, U.S. Pat. No. 4,848,331 by Northway-Mayer, U.S. Pat. No. 8,739,795 by Kanowitz, U.S. Pat. No. 10,040,231 by Nasir, U.S. Pat. No. 10,492,228 by Reddy et al., U.S. Pat. No. 10,709,858 by McDonald, and U.S. Patent Application 2016/0082111 by Chedid et al. While these various patient masks may have been generally satisfactory, there is nevertheless a need for a new and improved patient endoscopy mask.

The preferred patient endoscopy mask, according to various embodiments of the present invention, offers the following advantages: ease of use; lightness in weight; durability; the ability to use the mask for upper G.I. endoscopy and extubation; the use of a sleeve for covering the insertion tube of a gastroscope (upper G.I. endoscope) tube and prevent pathogens from contaminating the environment upon insertion and removal; the ability of the ET tube to provide oxygen and also function as a suction; the ability to provide negative pressure within the mask to prevent pathogens from escaping; the use of a viral filter to allow the negative pressure to draw air into the mask from the outside atmosphere without allowing pathogens to escape from the mask; the ability to use the mask in a variety of medical and non-medical settings; the use of filters to prevent the release of bacteria and viruses through patient breathing; the use of filters to further minimize the spread of infection to the healthcare providers; and the ability to provide multiple ports to connect to suction tubing and oxygen. In fact, in many of the preferred embodiments, these advantages are optimized to an extent that is considerably higher than heretofore achieved in prior, known patient masks.

It is a purpose of this invention to fulfill these and other needs in the patient endoscopy mask art in a manner more apparent to the skilled artisan once given the following disclosure.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION in order to address the shortcomings of the prior, known patient masks, it would be desirable to utilize a novel, single-use, lightweight, disposable, easy-to-use endoscopy mask that is secured around the patient's head and neck. It contains the spread of any respiratory pathogens during upper G.I. endoscopy procedure thereby allowing the gastroenterologist (doctor) to insert and withdraw the gastroscope (upper G.I. endoscope) through an opening in the mask. The mask can also be used for extubation thereby allowing the anesthesiologist to place the mask over the endo-tracheal tube ("ET tube") through an opening in the mask. The mask can be utilized for airway intervention to contain pathogens in the intensive care unit (ICU), emergency department (ED), operating room (OR), and the G.I. endoscopy suite. It can also potentially be utilized away from the hospital in ambulances, hospice care, and nursing homes. The endoscopy mask confines potentially dangerous airway secretions to a sealed area around the patient's nose and mouth. The mask may decrease the use of medical/surgical supplies which can be provided to other high-risk areas, decrease the cost of overall personal protective equipment (PPE), and provide lifesaving protection for healthcare workers involved in high risk pathogen aerosolizing procedures.

Figure 1:
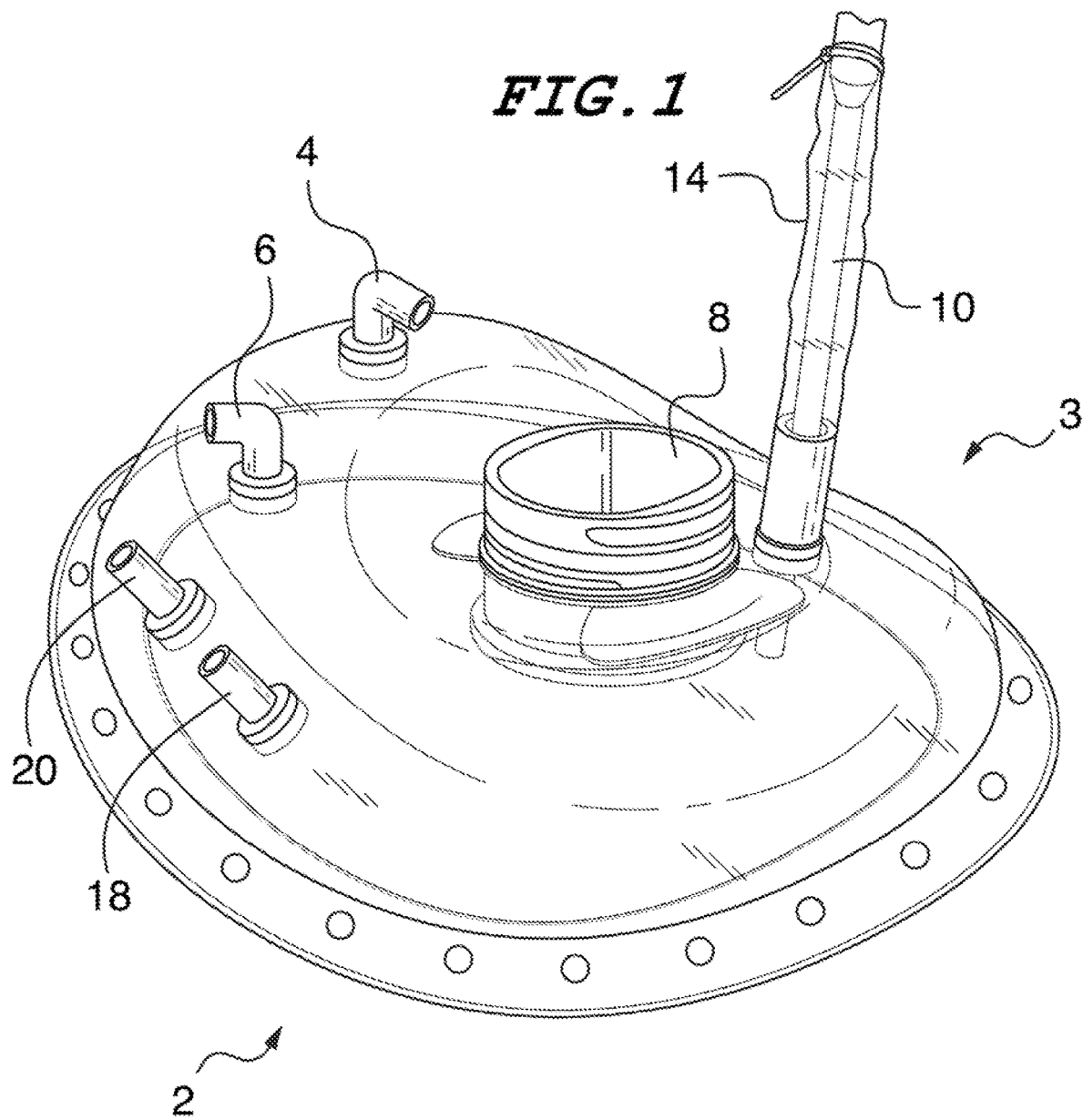
FIG. 1 is a schematic, isometric illustration of a patient endoscopy mask, constructed according the present invention.
Figure 2:
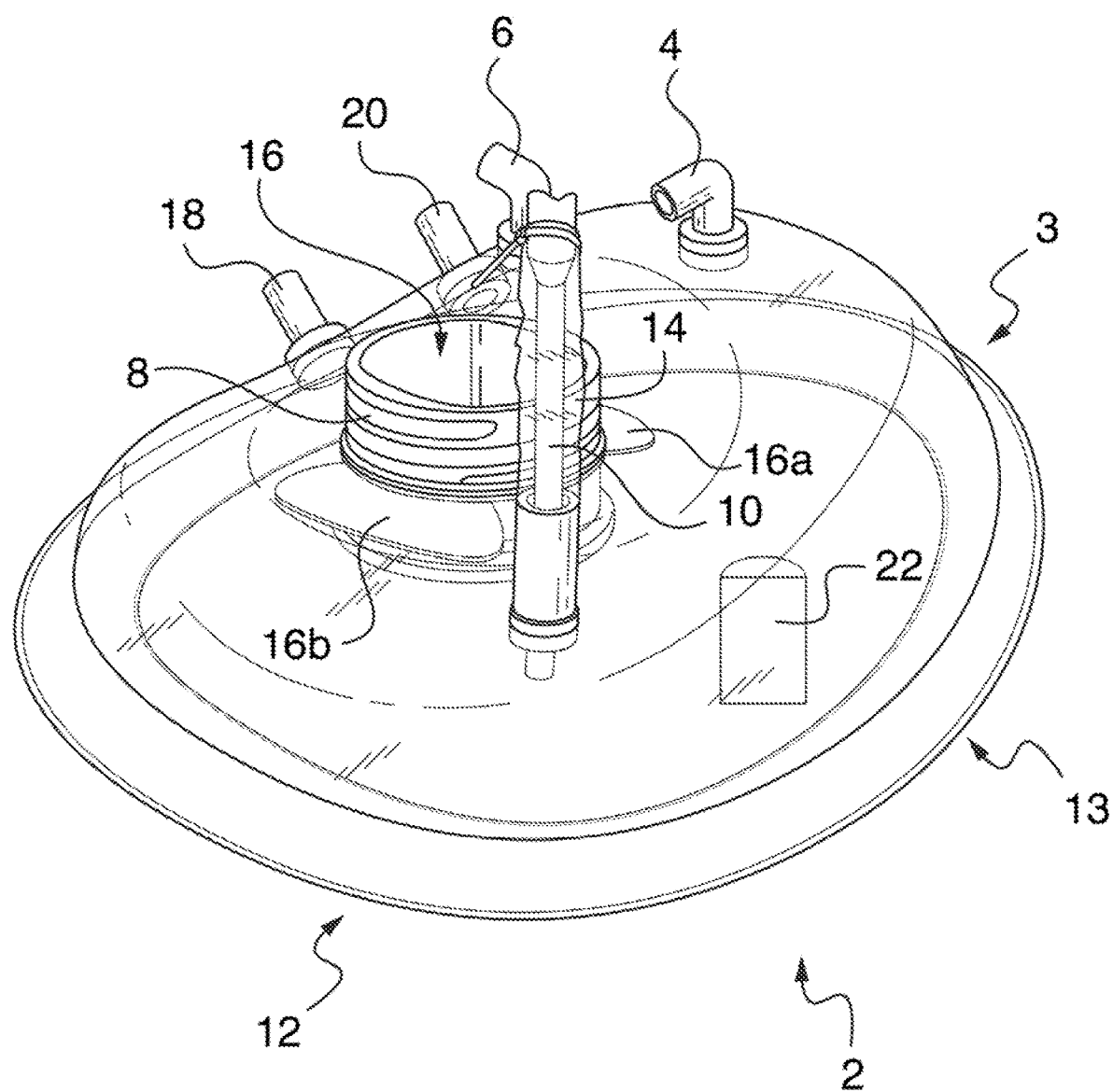
FIG. 2 is another schematic, isometric illustration of the patient endoscopy mask, constructed according the present invention.

Reference is made now to FIGS. 1 and 2, where there is illustrated a patient endoscopy mask 2, wherein the patient endoscopy mask 2 includes, in part, mask base 3, end tidal $CO_2$ sampling connection luer lock port 4, oxygen ($O_2$) connection port 6, endoscope entrance port 8, integrated flexible suction tip 10, pliable plastic sheath 12, foam cushion 13, suction tip sleeve 14, integrated bite block 16, in-line filter suction connection luer lock port 18, oxygen ($O_2$) connection port for bag ventilation 20, and viral filter 22. Preferably, mask base 3, end tidal $CO_2$ sampling connection luer lock port 4, oxygen ($O_2$) connection port 6, endoscope entrance port 8, integrated flexible suction tip 10, integrated bite block 16, in-line filter suction connection luer lock port 18, and oxygen ($O_2$) connection port 20 are constructed of any suitable, durable, UV resistant, high strength, lightweight, and medical grade material. Also, pliable plastic sheath 12 and suction tip sleeve 14, preferably, are constructed of any suitable, durable, UV resistant, high strength, lightweight, flexible, transparent medical grade material.

With respect to end tidal $CO_2$ sampling connection luer lock port 4, it is to be understood that end tidal $CO_2$ sampling connection luer lock port 4 may be a snug fit or any other type of connector. The end tidal $CO_2$ sampling connection luer lock port 4 is located near the patient's nasal openings for optimal sampling. Also, end tidal $CO_2$ sampling connection luer lock port 4 can be angled to provide for optimal exposure to connect a conventional $CO_2$ sampling line (not shown) as the patient is lying on his/her left side for a gastroscopy procedure. Finally, the $CO_2$ sampling line may then be connected to a conventional $CO_2$ monitor (not shown) which may also be part of the anesthesia machine.

With respect to oxygen ($O_2$) connection port 6, oxygen ($O_2$) connection port 6 is used for supplying oxygen during the gastroscopy. It may be a connector of any type that provides a tight seal. The oxygen ($O_2$) connection port 6 may be placed on the right side of the mask 2 near the patient's nose for optimal oxygenation to the nose and also optimal exposure as the patient is lying on the left side for a gastroscopy procedure.

With respect to endoscope entrance port 8, endoscope entrance port 8 may include a luer or any tight connector fitting to attach a sleeve 56 (FIG. 4) to mask 2 at one end and the endoscope's boot 254 (FIG. 12) at the other end, thereby allowing the endoscope scope 250 (FIG. 14) to go in and out of the patient's esophagus and stomach while limiting pathogens from escaping during the procedure.

With respect to integrated flexible suction tip 10, integrated flexible suction tip 10 provides a connection for negative pressure to be introduced into the mask 2 in order to decrease pathogens from escaping from the mask 2 and also for providing suctioning of saliva from the patient during the procedure. Preferably, the integrated flexible suction tip 10 is placed on the left side of the mask 2 (but can be on either side) near the endoscope entrance portal 8 to prevent saliva from pooling on the left side of the patient's mouth from gravity as the patient is lying on his/her left side during a gastroscopy procedure.

With respect to pliable plastic sheath 12, pliable plastic sheath 12 includes foam 13 located on the inside of the sheath 12 such that foam 13 is attached around the mask 4 and the foam 13 and the sheath 12 will lay on the patient's face with the sheath 12 laying directly on the patient's face. The pliable plastic sheath 12 acts as a protective barrier to decrease pathogens from escaping the mask 2 while mask 2 is attached to the patient's face. As will be discussed in greater detail later, an adhesive gel layer 26 (FIG. 3) is located between the sheath 12 and the patient's face to further prevent pathogens from escaping the mask 2. The foam 13 on the inside of the mask 2 will allow the sheath 12 to adapt to many different facial features in that the foam 13 will compress at high points like the bridge of the nose and fill out to form fit the lower points of the patient's face. There will be holes 15 (FIG. 3) in the sheath 12 to allow air to escape as needed so that the foam 13 can compress or refill, thereby allowing the foam 13 to expand. Pliable plastic sheath 12 may also be a balloon type which is typically found on other oxygen O2 masks.

With respect to foam cushion 13, a unique aspect of the present invention is that foam cushion 13 will allow the sheath 12 to adapt to many different facial features of the patient. Furthermore, foam cushion 13, preferably, is constructed of a polymeric material that will compress at high points like the bridge of the patient's nose and fill out to form fit the lower points of the patient's face. Finally, there will be holes 15 (FIG. 3) in the sheath 12 to allow air to escape as needed so that the foam cushion 13 can compress or refill, thereby allowing the foam cushion 13 to expand.

With respect to suction tip sleeve 14, suction tip sleeve 14 encapsulates integrated flexible suction tip 10 in order to allow the suction tip 10 to go through the mask 2 and into the patient's mouth for suctioning saliva from the patient, and also coming back out of the mask 2 while keeping pathogens within the mask 2.

Figure 3:
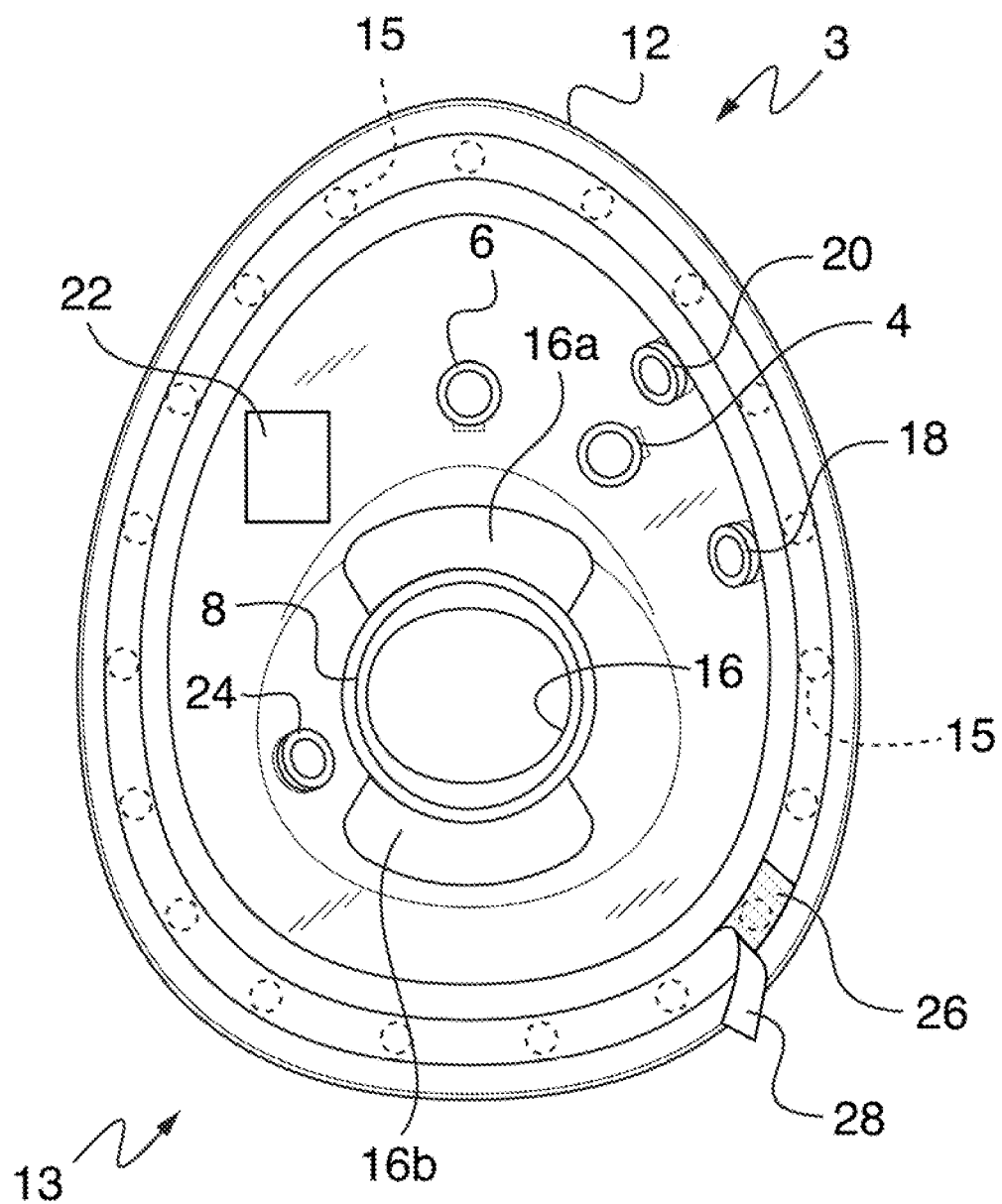
FIG. 3 is a schematic illustration of the underside of the patient endoscopy mask, constructed according the present invention.

With respect to integrated bite block 16, integrated bite block 16 is used for a gastroscopy procedure. Bite block 16 is connected to the inside of the mask 2 at an optimal position to allow the patient's teeth to sit at the top part 16a and the bottom part 16b of the bite block 16 (FIG. 3). This allows the endoscope insertion tube 252 (FIG. 14) to be inserted into the patient's mouth and prevent the patient from biting down onto the endoscope insertion tube. Furthermore, another unique aspect of the present invention is that this integrated design of the bite block 16 also decreases pathogens from escaping the mask 2.

With respect to in-line filter suction connection luer lock port 18, it is to be understood that in-line filter suction connection luer lock port 18 may be a snug fit or any other type of connector. Also, in-line filter suction connection luer lock port 18 can be connected to a conventional in-line filter suction line (not shown). Finally, the in-line filter suction line may then be connected to a conventional suction device (not shown) which may also be part of the anesthesia machine.

With respect to oxygen ($O_2$) connection port 20, oxygen ($O_2$) connection port for bag ventilation 20 may also be used for supplying oxygen during the gastroscopy. It may be a connector of any type that provides a tight seal. The oxygen ($O_2$) connection port 20 is placed on the left side of the mask near the nose for optimal oxygenation to the nose and also optimal exposure as the patient is lying on his/her left side for a medical procedure.

With respect to viral filter 22, viral filter 22 allows for air exchange from outside of mask 2 and inside of mask 2, while keeping pathogens within mask 2. This is especially important when negative pressure is being used within the mask 2.

Regarding FIG. 3, the underside of mask 3 is illustrated. In particular, mask base 3, endoscope entrance port 8, integrated flexible suction tip 10, pliable plastic sheath 12, foam cushion 13, suction tip sleeve 14, integrated bite block 16, bite block top portion 16a, bite block bottom portion 16b, viral filter 22, bite block ring 24, adhesive gel layer 26, and adhesive gel layer barrier 28 are shown.

With respect to bite block ring 24, bite block ring 24, preferably, is constructed of any suitable, durable, UV resistant, high strength, lightweight, and medical grade material. It is to be understood that bite block ring 24 is attached to the left side (but could be on either side) of the bite block 16 to ensure that that the suction tip 10 will stay in the same entry point by the patient's mouth every time.

With respect to adhesive gel layer 26, adhesive gel layer 26, preferably, includes any suitable, UV resistant, medical grade adhesive gel that will create a barrier to prevent pathogens from escaping from the mask 2 around the area where the plastic sheath 12 and the foam cushion 13 contact the patient's face.

With respect to adhesive gel layer barrier 28, adhesive gel layer barrier 28 is constructed of any suitable, durable, UV resistant, high strength, lightweight, and medical grade material. It is to be understood that adhesive gel layer barrier 28 is placed over adhesive gel layer 26 to prevent adhesive gel layer 26 from being contaminated by foreign substances prior to mask 2 being used. Once mask 2 is ready to be attached to the patient, the adhesive gel layer barrier 28 is conventionally removed so that adhesive gel layer 26 is exposed.

Figure 4:
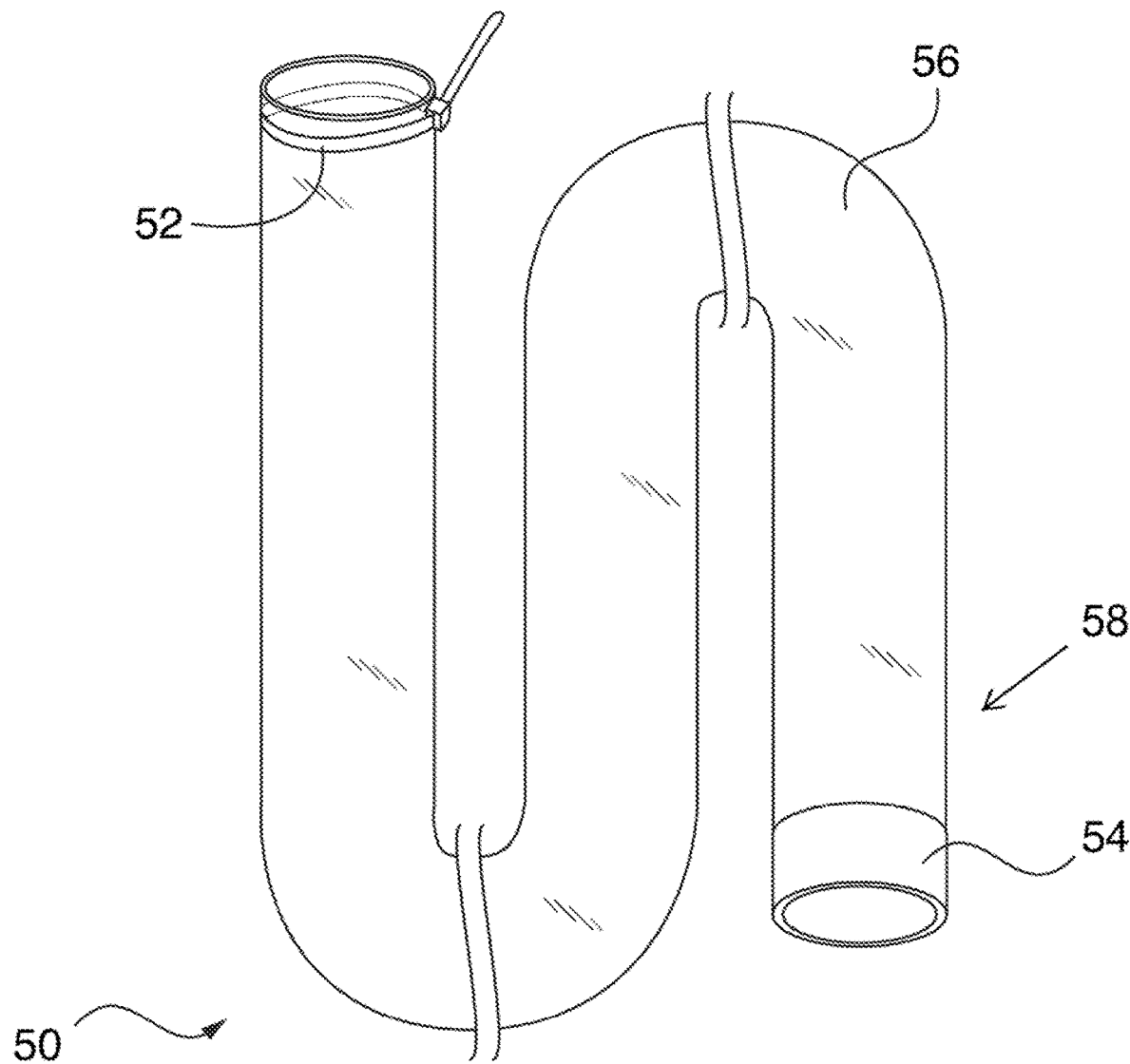
FIG. 4 is a schematic illustration of a sleeve for covering the endoscope insertion tube, constructed according the present invention.

As shown in FIG. 4, there is illustrated sleeve assembly 50. Sleeve assembly 50, includes, in part, sleeve connector 52, sleeve connector 54, endoscope sleeve 56, and sleeve distal areas 58. Preferably, sleeve connector 52 and sleeve connector 54 are constructed of any suitable, durable, UV resistant, high strength, lightweight, and medical grade material. Also, endoscope sleeve 56 is constructed of any suitable, durable, UV resistant, flexible, high strength, lightweight, transparent, and medical grade material.

Figure 12:
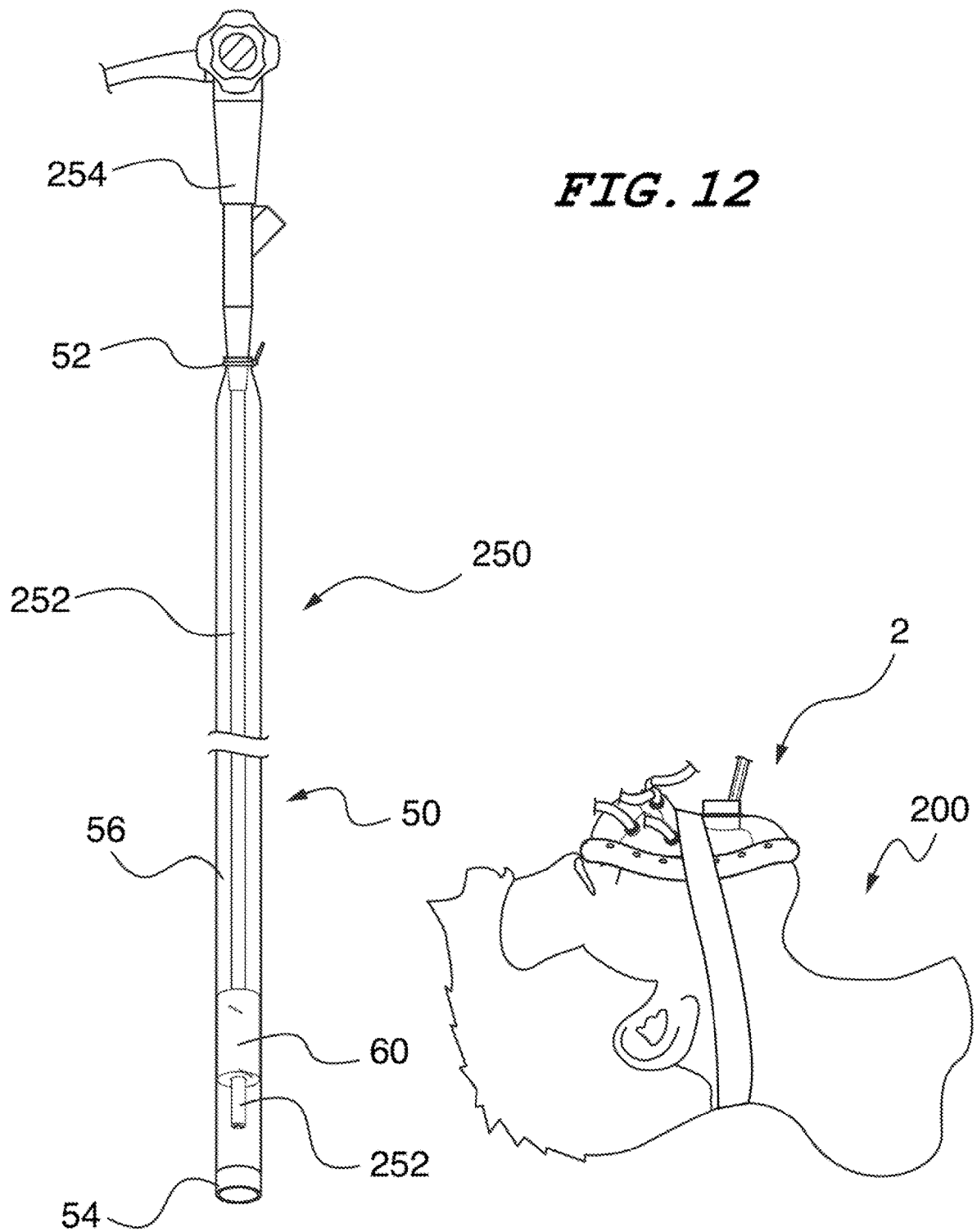
FIG. 12 is a schematic side view of the sleeve being completely located on the endoscope insertion tube and prior to the endoscope insertion tube being placed into the patient, according the present invention.

With respect to sleeve connector 52, sleeve connector 52 is connected to the distal end of the endoscope sleeve 56. Also, sleeve connector 52 should be constructed so that sleeve connector 52 tightly fits the endoscope's boot 254 (FIG. 12). It is to be understood that endoscope sleeve 56 may also be connected to the endoscope's boot 254 by adhesive tape, clamps, or other similar tightening devices.

Regarding sleeve connector 54, sleeve connector 54 is attached to the proximal end of the endoscope sleeve 56. In this manner, sleeve connector 54 can be used to connect endoscope sleeve 56 to endoscope entrance port 8 through the use of sleeve connector 54. It is to be understood that endoscope sleeve 56 may also be connected to endoscope entrance port 8 by conventional luer locks, clips, or any other fastening devices that will properly attach the endoscope sleeve 56 to the endoscope entrance port 8 and not allow pathogens to escape the mask 2 or endoscope sleeve 56.

Regarding endoscope sleeve 56, endoscope sleeve 56 is constructed to slide over the insertion tube 252 (FIG. 12) of the endoscope to keep pathogens within the endoscope sleeve 56. It is to be understood that endoscope sleeve 56 is attached to sleeve connector 52 on the distal end of endoscope sleeve 56 and sleeve connector 54 on the proximal end of endoscope sleeve 56, as discussed above.

Figure 5:
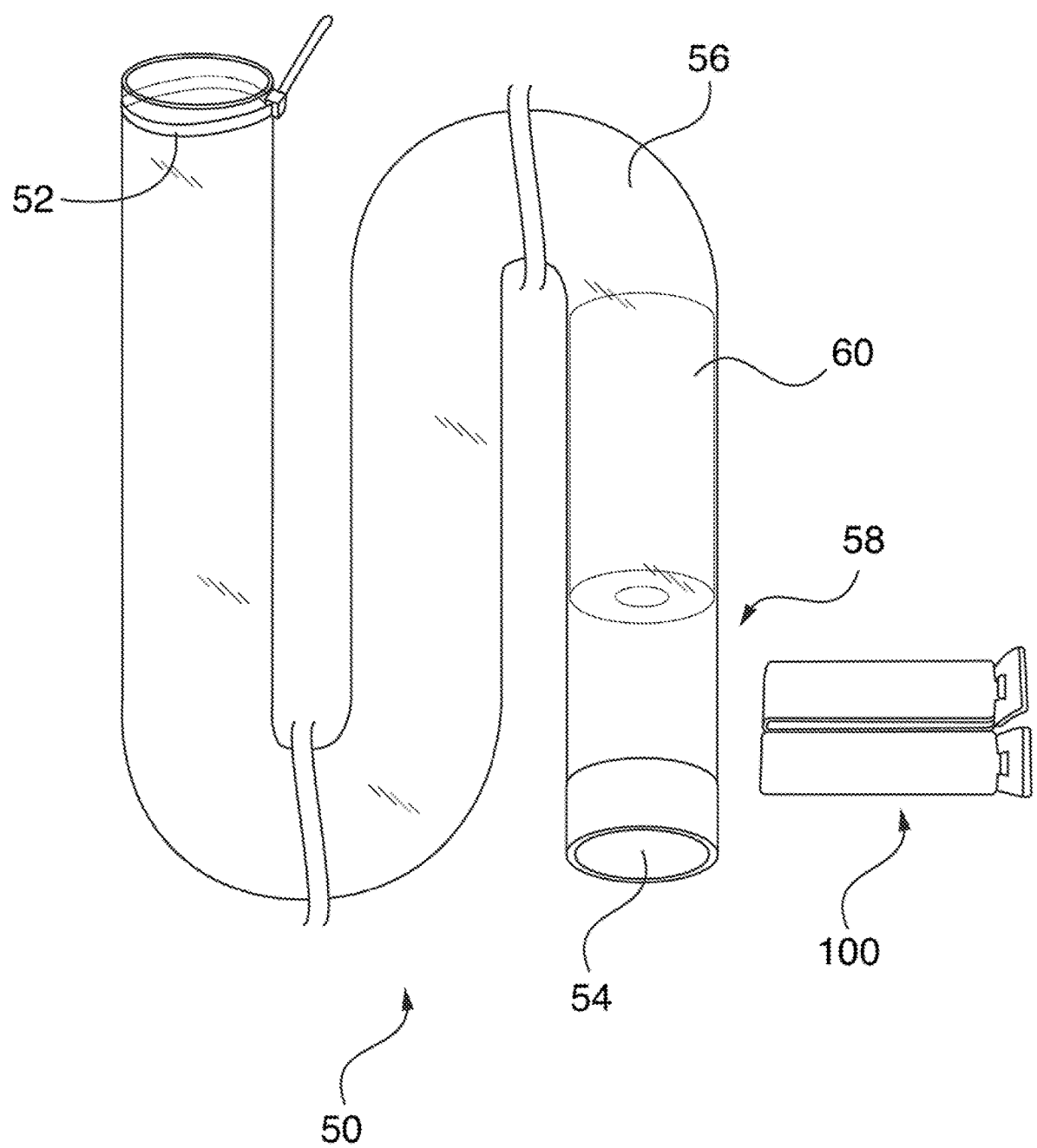
FIG. 5 is another schematic illustration of the sleeve for covering the endoscope insertion tube, constructed according the present invention.

With respect to FIG. 5, there is illustrated a more detailed view of sleeve assembly 50. As shown in FIG. 5, sleeve assembly 50, includes, in part, sleeve connector 52, sleeve connector 54, endoscope sleeve 56, sleeve distal areas 58, sponge 60, and double clip assembly 100.

Regarding sponge 60, sponge 60, preferably, is constructed of any suitable, durable, UV resistant, absorbent, lightweight, and medical grade material. It is to be understood that sponge 60 should be positioned within the endoscope sleeve 56 so as to meet the tip of the endoscope insertion tube 252 (FIG. 12) when connector 52 is secured at the endoscope's boot 254 (FIG. 12). A unique aspect of the present invention is that the sponge 60 can be used for soaking up detergent at the end of the procedure to wipe down the insertion tube 252 (FIG. 11) of the endoscope 250. In this manner, incorporating sponge 60 into endoscope sleeve 56 makes the endoscope sleeve 56 compliant with universal protocols of cleaning the endoscope 250 at bedside from the Society of Gastroenterology Nurses & Associates (SGNA) guidelines and manufacturers I.F.U. (Instructions for Use) for cleaning.

Figure 6:
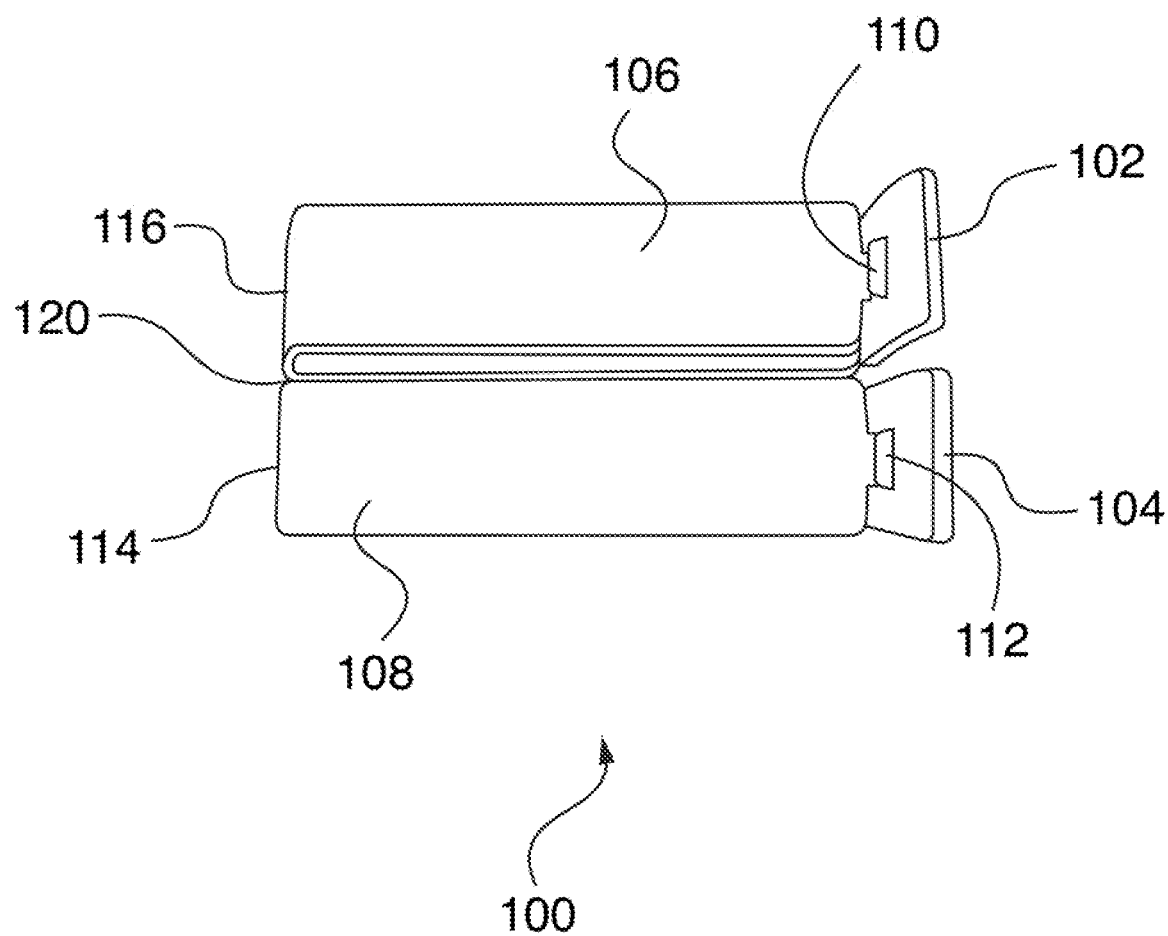
FIG. 6 is a schematic illustration of a double clip, constructed according the present invention.

With respect to FIGS. 5 and 6, there are illustrated double clip assembly 100. Double clip assembly 100, preferably, is constructed of any suitable, durable, UV resistant, high strength, lightweight, and medical grade material. As more clearly shown in FIG. 6, double clip assembly 100, includes, in part, levers 102, 104, clip arms 106, 108, latches 110, 112, hinges 114, 116, and clip separator 120.

As will be discussed in greater detail later, double clip assembly 100 clips between the mask 2 and the endoscope insertion tube 252 (FIG. 16) once the endoscope insertion tube 252 has been withdrawn from the patient's mouth. Once the double clip assembly 100 is placed in the appropriate position (e.g., location 58) on endoscope sleeve 56, double clip assembly 100 may be cut at clip separator 120 to allow the portion of the endoscope insertion tube 252 contained within the endoscope sleeve 56 to be separated from the endoscopy mask 2 while still securing both ends endoscope sleeve 56 so that pathogens are not allowed to escape.

In particular, in order to secure double clip assembly 100 to endoscope sleeve 56 at location 58, the end user pulls on levers 102 and 104. The end user then pulls on clip arms 106 and 108 so that clip arms 106 and 108 pivot upwardly around hinges 116 and 114, respectively. The end user locates the clip assembly 100 at or near location 58 by placing that portion of endoscope sleeve 56 underneath clip arms 106 and 108. The end user then pushes down on clip arms 106 and 108 so that ends of clip arms 106 and 108 interact with latches 110 and 112, respectively. The end user then presses the ends of clip arms 106 and 108 so that clip arms 106 and 108 "click into place" with latches 110 and 112, respectively. In this manner, clip arms 106 and 108 are securely held in place by latches 110 and 112, respectively, so that portion of endoscope sleeve 56 at location 58 is securely retained by clip arms 106 and 108.

A unique aspect of the present invention is that double clip assembly 100 may be cut at clip separator 120 to allow the portion of the endoscope insertion tube 252 (FIG. 18) contained within the endoscope sleeve 56 to be separated from the endoscopy mask 2 while still securing both ends of endoscope sleeve 56 so that pathogens are not allowed to escape.

Figure 7:
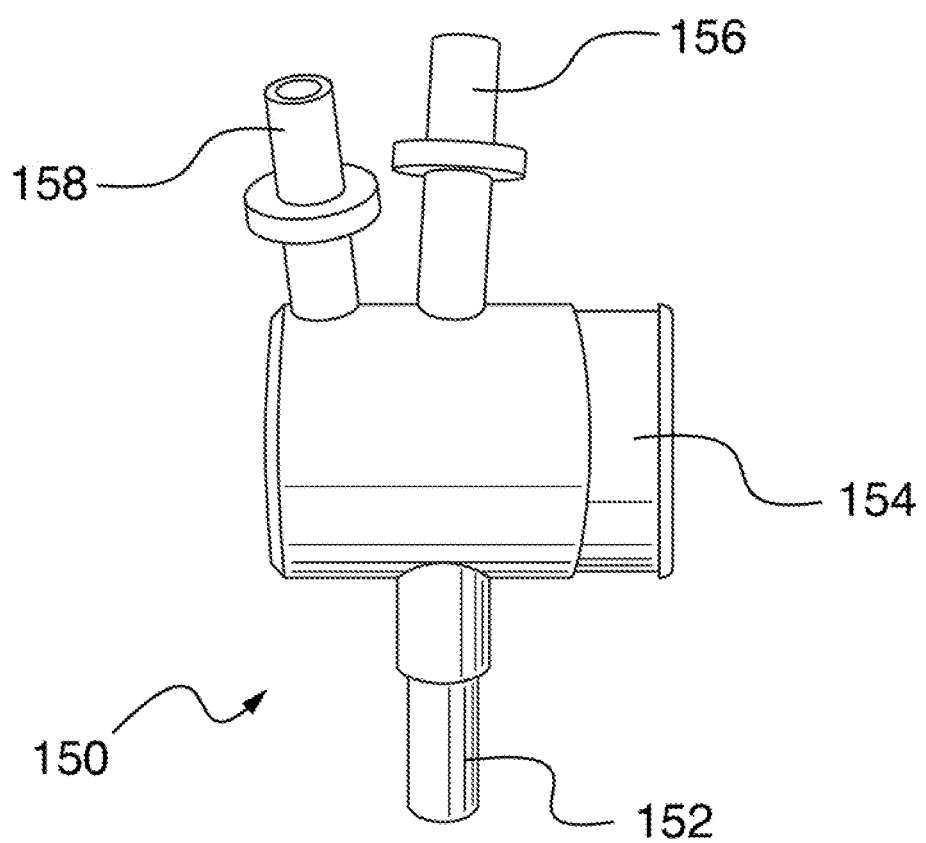
FIG. 7 is a schematic illustration of an oxygen/suction connector, constructed according the present invention.
Figure 10:
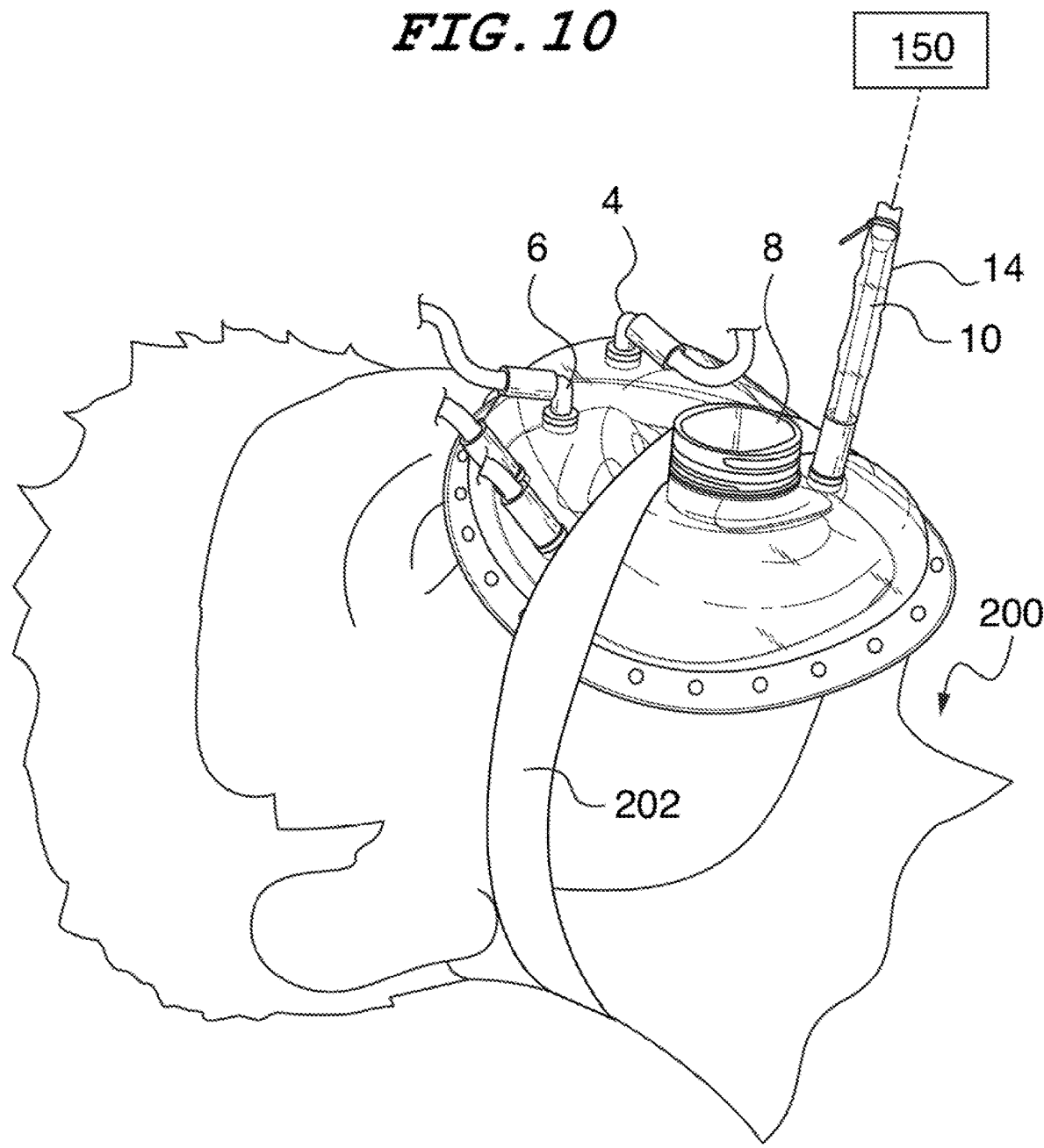
FIG. 10 is a schematic top view of the endoscopy mask being strapped around a patient's face, according the present invention.

With respect to FIG. 7, there is illustrated $O_2$ connector assembly 150. $O_2$ connector assembly 150, includes, in part, endotracheal tube/suction tube connection port 152, oxygen/suction button 154, oxygen connection port 156, and suction connection port 158. Preferably, endotracheal tube/suction tube connection port 152, oxygen/suction button 154, oxygen connection port 156, and suction connection port 158 are constructed of any suitable, durable, UV resistant, high strength, lightweight, and medical grade material. It is to be understood that endotracheal tube/suction tube connection port 152 is attached to the suction tip 10 or an ET tube (FIG. 10). Also, suction connection port 158 is conventionally attached to a conventional suction device (not shown). Finally, oxygen connection port 156 is conventionally attached to an oxygen providing device (not shown).

Another unique aspect of the present invention is that $O_2$ connector assembly 150 will continuously provide oxygen from an oxygen source and will also immediately switch to suction once the button 154 on the $O_2$ connector assembly 150 is pressed down. Once the button 154 is released, $O_2$ connector assembly 150 will automatically switch back to providing oxygen. This feature provides the ability to suction up any saliva or blood from the patient and can also be used to supplement the patient with oxygen again after suction usage.

Figure 8:
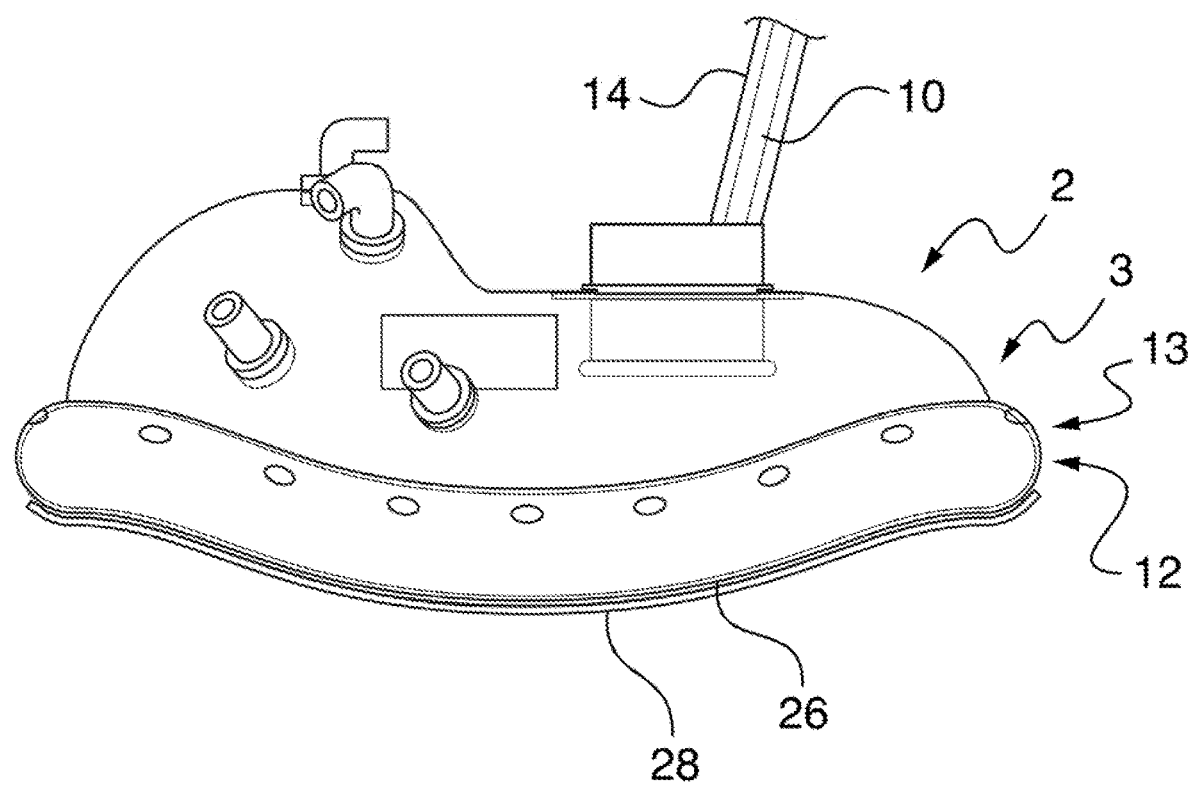
FIG. 8 is a schematic side view of the plastic sheath with foam which are attached around the underside of the mask, constructed according the present invention.

With respect to FIG. 8, there is illustrated a side view of mask 3. In particular, mask base 3, pliable plastic sheath 12, foam cushion 13, adhesive gel layer 26, and adhesive gel layer barrier 28 are shown.

As discussed above, adhesive gel layer 26, preferably, includes any suitable, UV resistant, medical grade adhesive gel that will create a barrier to prevent pathogens from escaping from the mask 2 around the area where the plastic sheath 12 and the foam cushion 13 contact the patient's face.

As discussed above, adhesive gel layer barrier 28 is constructed of any suitable, durable, UV resistant, high strength, lightweight, and medical grade material. It is to be understood that adhesive gel layer barrier 28 is placed over adhesive gel layer 26 to prevent adhesive gel layer 26 from being contaminated by foreign substances prior to the mask 2 being used. Once mask 2 is ready to be attached to the patient, the adhesive gel layer barrier 28 is conventionally removed so that adhesive gel layer 26 is exposed.

Method of Using Endoscopy Mask

Figure 9:
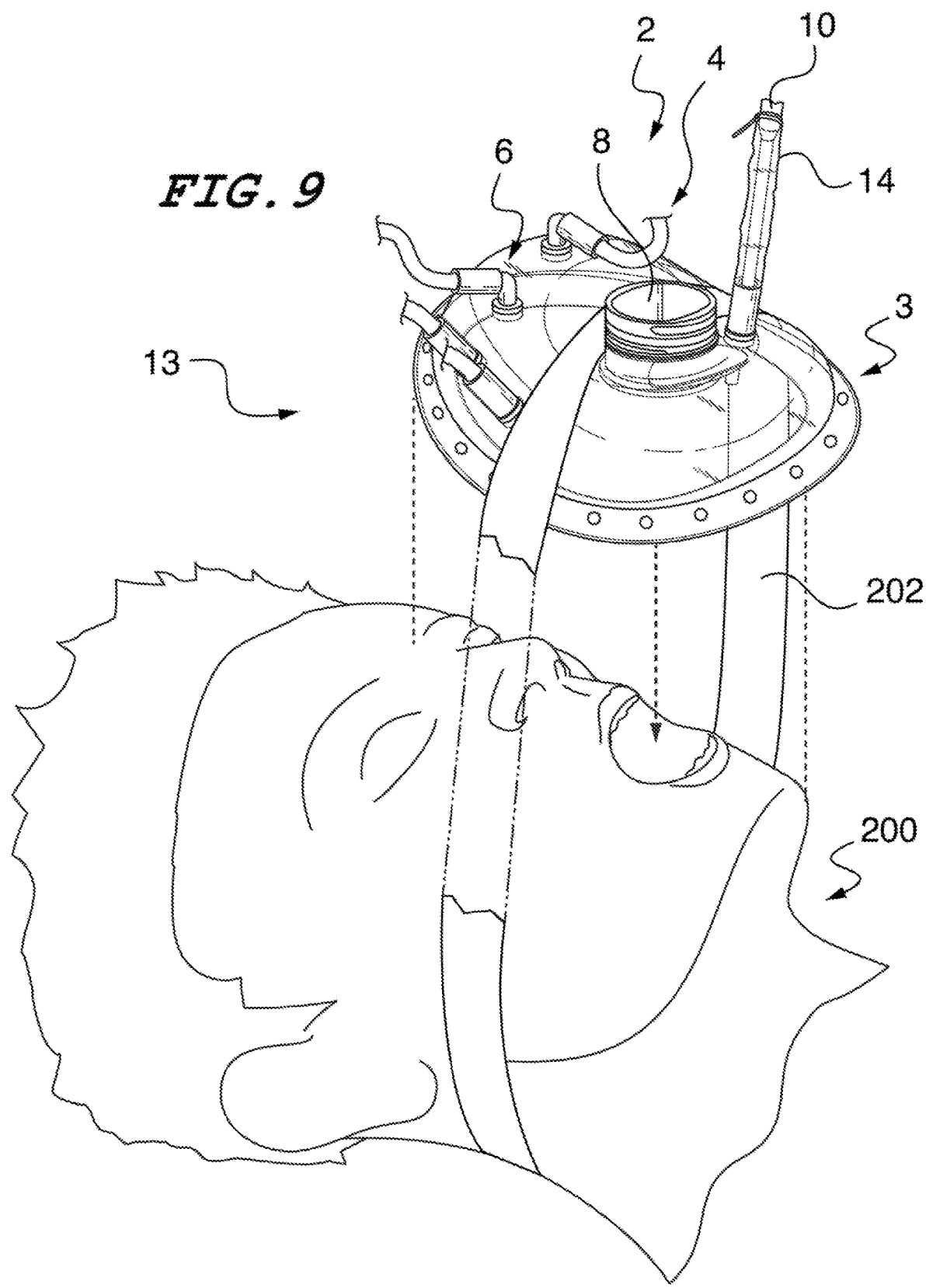
FIG. 9 is a schematic side view of the endoscopy mask being strapped around a patient's face, according the present invention.

With respect to the method of using endoscopy mask 2 and with reference to FIGS. 1-19, assume that an adult male (patient 200 as shown in FIG. 9) arrives in the endoscopy suite with COVID-19 and a progressive esophageal varices bleed requiring urgent upper G.I. endoscopy. Routine principles of G. endoscopy are followed to include personal protective equipment (PPE) such as mask, gloves, eye protection, and gown. It is to be understood that medical treatment consent of the patient 200 should be obtained, when possible.

The gastroenterologist then procures the appropriate equipment for an upper G.I. endoscopy. It is to be understood that the equipment may include a video G.I endoscopic tower system, a single or double channel endoscope, esophageal banding kits, endoscopic clips, and a suction tip connected to a suction unit.

As shown in FIGS. 9 and 10, the patient 200 is placed in a supine position but may also be lying on the left. Once mask 2 is ready to be attached to the patient 200, the adhesive gel layer barrier 28 is conventionally removed so that adhesive gel layer 26 is exposed, as discussed above. The patient endoscopy mask 2 is positioned over the patient's head and neck and secured to the patient's head and neck through the use of mask strap 202 (FIG. 9). The end tidal $CO_2$ sampling connection luer lock port 4 is conventionally connected to an end tidal $CO_2$ sampling device (not shown). The oxygen ($O_2$) connection port 6 is conventionally connected to an oxygen device (not shown). The integrated flexible suction tip 10 is conventionally connected to a suction device (not shown). The in-line filter suction connection luer lock port 18 is conventionally connected to an in-line filter suction device (not shown). Finally, the $O_2$ connector assembly 150 is attached to the suction tip 10 or an ET tube.

Figure 11:
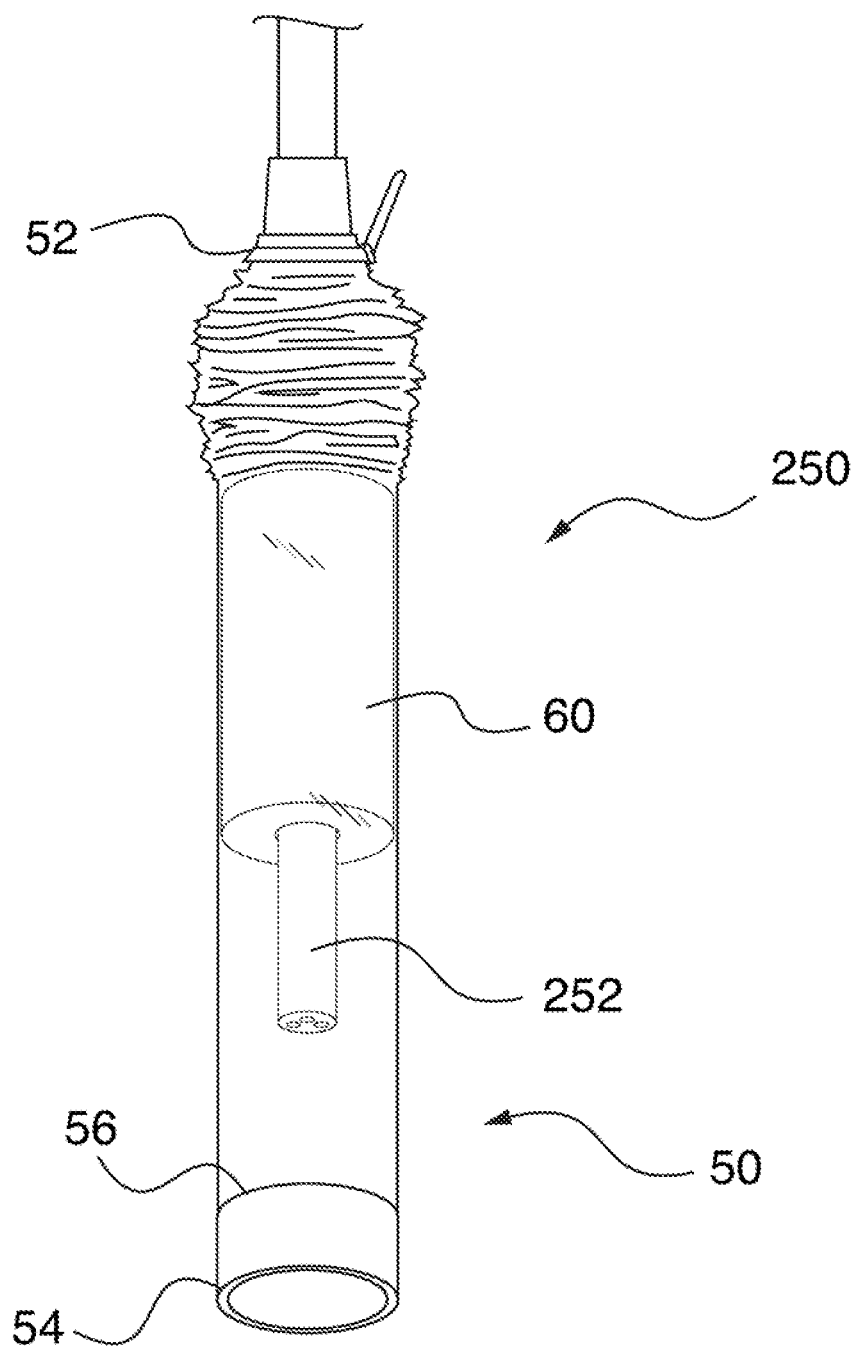
FIG. 11 is a schematic side view of the sleeve initially being located on the endoscope insertion tube, according the present invention.

With respect to FIG. 11, the lower end of endoscope assembly 250 is illustrated. The lower end of endoscope assembly 250 includes, in part, conventional insertion tube 252. As shown in FIG. 11, insertion tube 252 has been located within endoscope sleeve 56 and sponge 60.

With respect to FIG. 12, the endoscope sleeve 56 has been slid along the length of insertion tube 252. Also, sleeve connector 52 has been connected to endoscope boot 254. In this manner, endoscope assembly 250 is ready to be used on patient 200.

Figure 13:
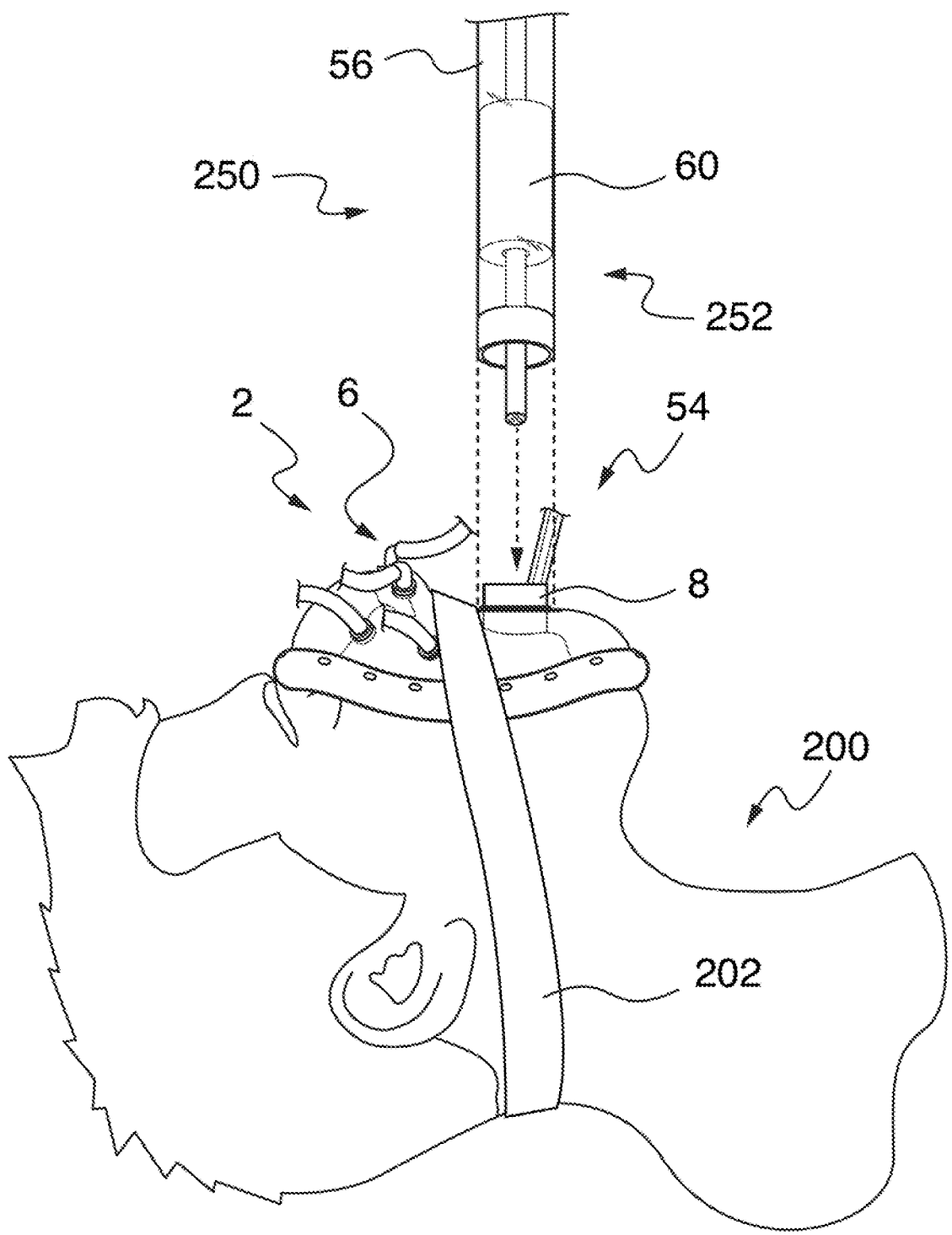
FIG. 13 is a schematic side view of the sleeve being completely located on the endoscope insertion tube and the endoscope insertion tube being placed into the patient, according the present invention.
Figure 14:
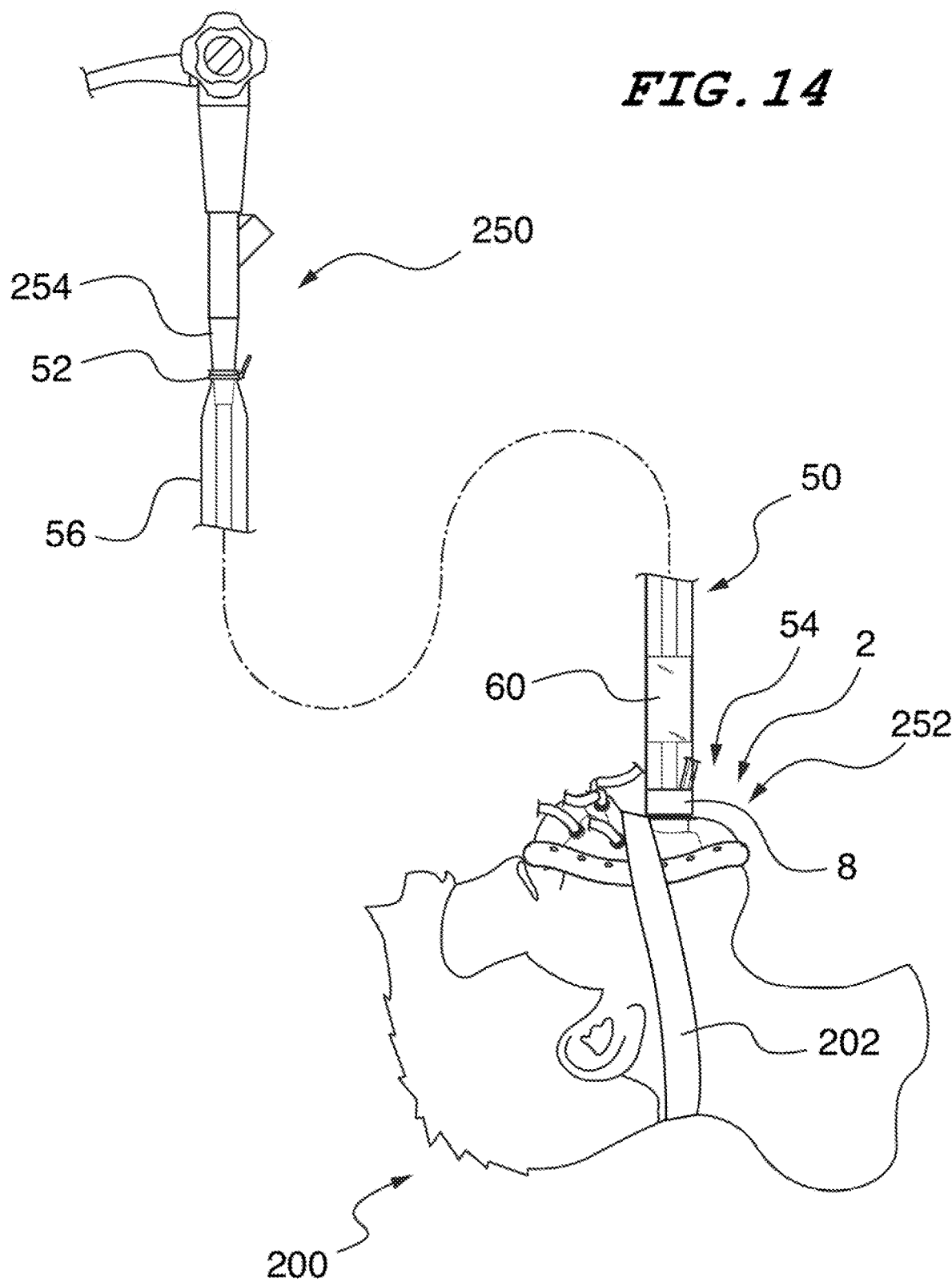
FIG. 14 is a schematic side view of the sleeve connector being attached to the endoscopy mask, according the present invention.

With respect to FIGS. 13 and 14, mask 2 has been attached to patient 200 and sleeve connector 54 has been attached to endoscope entrance port 8. As discussed earlier, sleeve connector 52 has been connected to endoscope boot 254. Once sleeve connector 54 has been attached to endoscope entrance port 8, insertion tube 252 is inserted into the patient 200. Another unique aspect of the present invention is that since sleeve connector 54 has been attached to endoscope entrance port 8 and sleeve connector 52 has been connected to endoscope boot 254, this creates a sealed environment for insertion tube 252 so that any pathogens that may expelled by patient 200 onto insertion tube 252 will be contained within endoscope sleeve 56.

Figure 15:
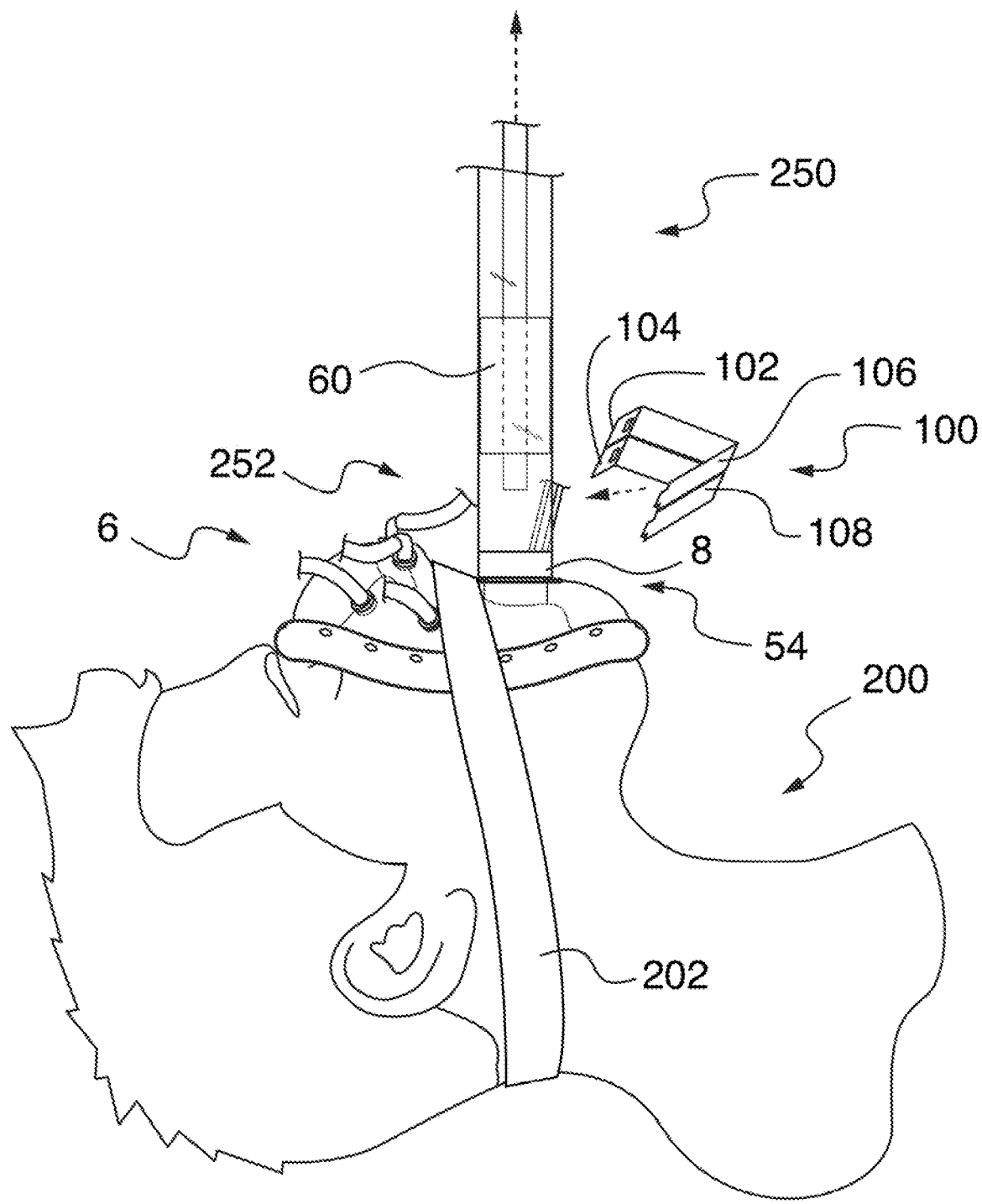
FIG. 15 is a schematic side view of the double clip being attached to the sleeve after the endoscope insertion tube has been removed from the patient, according the present invention.

With respect to FIG. 15, once the medical procedure has been completed on the patient 200 and the insertion tube 252 has been removed from the patient 200, sponge 60 can be used for soaking up detergent at the end of the procedure to wipe down the insertion tube 252 of the endoscope 250, as discussed earlier.

With respect to FIG. 15, once the insertion tube 252 has been removed from the mouth of patient 200, the double clip assembly 100 is clipped between the mask 2 and the end of insertion tube 252 on endoscope sleeve 56. The double clip assembly 100 is dipped onto the endoscope sleeve 56, as described earlier.

Figure 16:
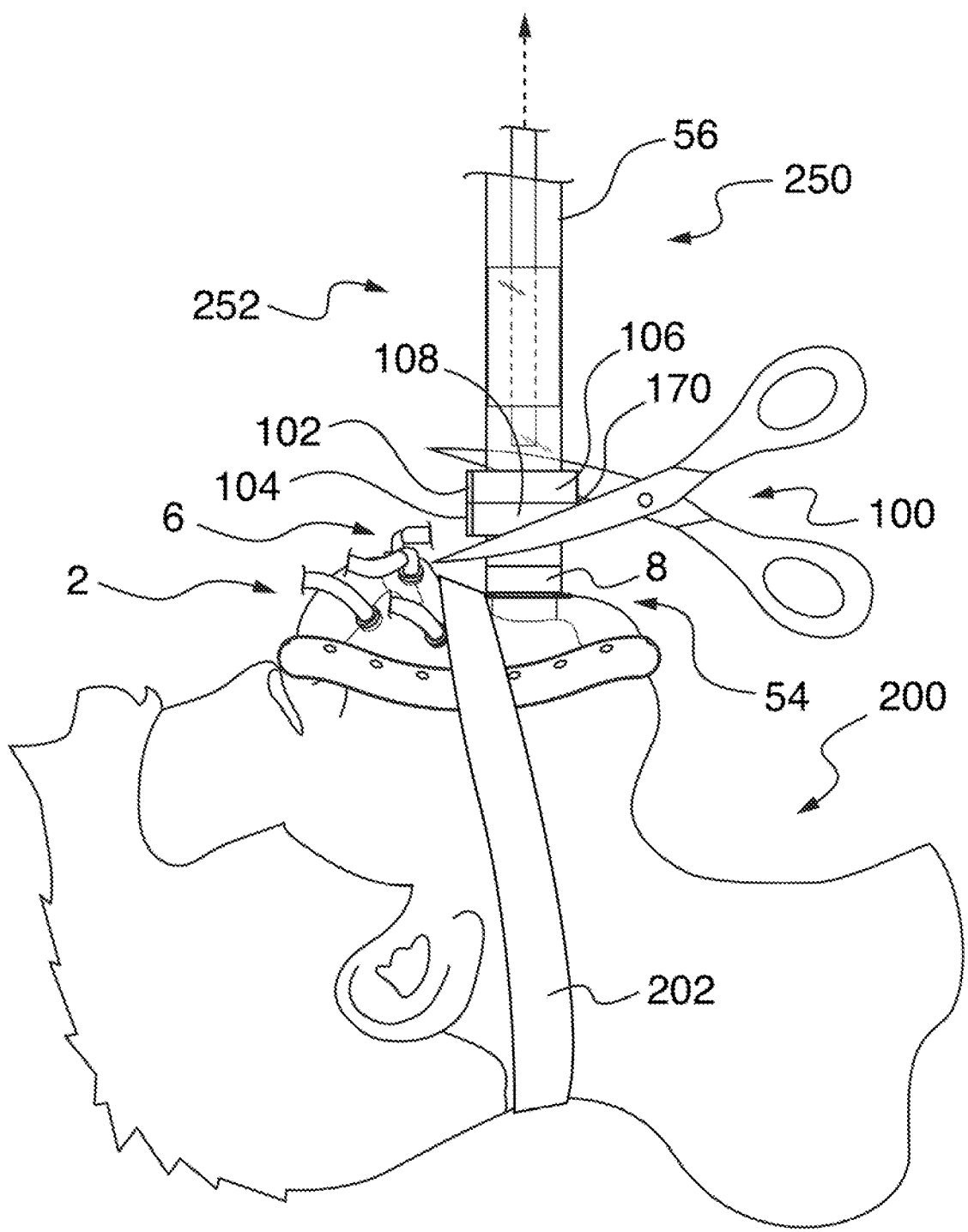
FIG. 16 is a schematic side view of the sleeve being cut through the double clip after the endoscope insertion tube has been removed from the patient, according the present invention.
Figure 17:
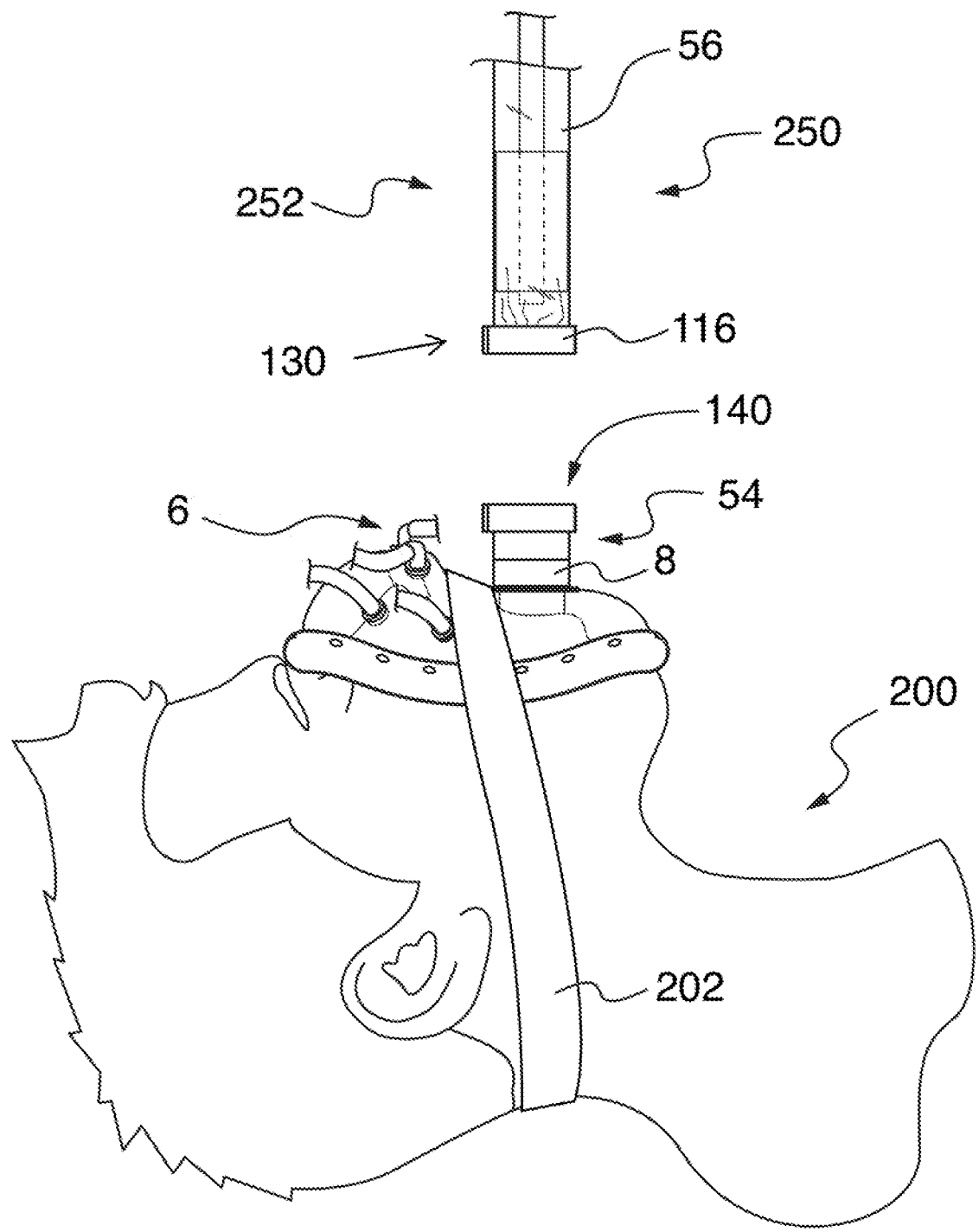
FIG. 17 is a schematic side view of the sleeve after the sleeve has been cut and the double clip is cut into two (2) pieces, according the present invention.

With respect to FIGS. 16 and 17, once the double clip assembly 100 is placed between the mask 2 and the end of insertion tube 252 on endoscope sleeve 56, double clip assembly 100 may be cut at clip separator 120 to allow an upper portion 130 of double clip assembly 100 to become separated from a lower portion 140 of double clip assembly 100. It is to be understood that upper portion 130 of double clip assembly 100 includes lever 102, clip arm 106, latch 110, and hinge 116. It is to be understood that lower portion 140 of double clip assembly 100 includes lever 104, clip arm 108, latch 112, and hinge 114. In this manner, once upper portion 130 and lower portion 140 are separated, since the end of endoscope sleeve 56 that is attached to upper portion 130 is closed because it is still sealed by to upper portion 130, any pathogens on insertion tube 252 are contained within endoscope sleeve 56 and are not allowed to escape.

Figure 18:
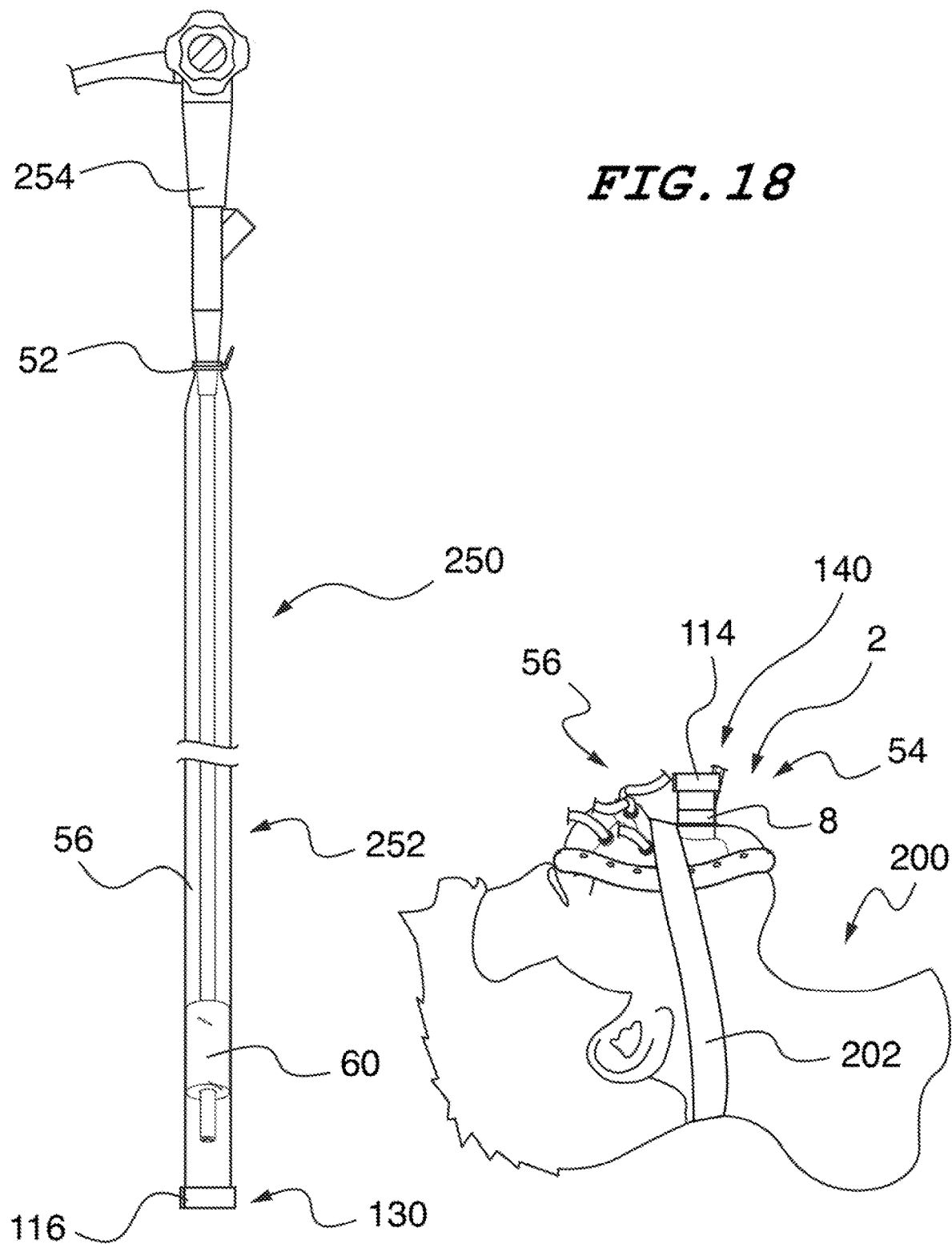
FIG. 18 is a schematic top view of a lower portion of the sleeve still attached to the endoscopy mask and a lower portion of the double clip being attached to the lower portion of the sleeve and the upper portion of the double clip being attached to the upper portion of the sleeve after the sleeve has been cut and the double clip is cut into two (2) pieces, according the present invention.

With respect to FIG. 18, the lower portion 140 of double clip assembly 100 is illustrated. As shown in FIG. 18, after double clip assembly 100 has been separated into upper portion 130 and lower portion 140, lower portion 140 remains attached to mask 2. Another unique aspect of the present invention is that even though double clip assembly 100 has been separated into upper portion 130 and lower portion 140 and endoscopy sleeve 56 has been cut, since the end of endoscope sleeve 56 that is attached to lower portion 140 is closed because it is still sealed by lower portion 140 and the sealed connection between endoscope entrance port 8 and sleeve connector 54, any pathogens being expelled by the patient 200 are contained within the mask 2 and are not allowed to escape.

With respect to FIG. 18, the upper portion 130 after the upper portion 130 and the lower portion 140 are separated. As shown in FIG. 18, since the end of endoscope sleeve 56 that is attached to upper portion 130 is closed and still sealed by to upper portion 130, any pathogens on insertion tube 252 are contained within endoscope sleeve 56 and are not allowed to escape.

With respect to FIG. 18, there is illustrated upper portion 130 and lower portion 140 after the upper portion 130 and the lower portion 140 are separated. As shown in FIG. 18, since the end of endoscope sleeve 56 that is attached to upper portion 130 is closed and still sealed by to upper portion 130, any pathogens on insertion tube 252 are contained within endoscope sleeve 56 and are not allowed to escape. Also, since the end of endoscope sleeve 56 that is attached to lower portion 140 is closed because it is still sealed by to lower portion 140 and the sealed connection between endoscope entrance port 8 and sleeve connector 54, any pathogens being expelled by the patient 200 are contained within the mask 2 and are not allowed to escape.

Figure 19:
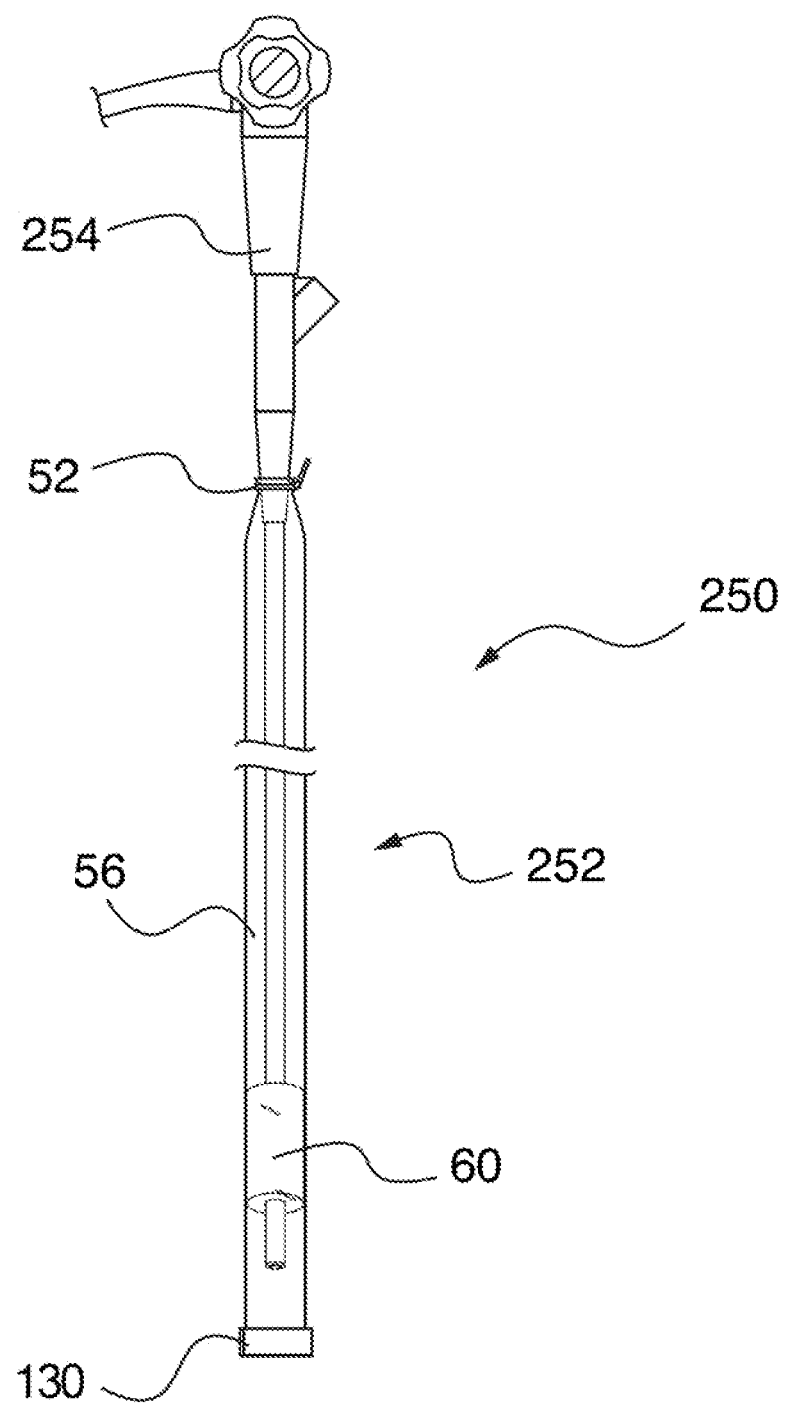
FIG. 19 is a schematic top view of the endoscope insertion tube being contained within the sleeve after the endoscope insertion tube has been removed from the patient and in preparation for transfer to a decontamination facility, according the present invention.

With respect to FIG. 19, as discussed above, since the end of endoscope sleeve 56 that is attached to upper portion 130 is closed and still sealed by upper portion 130, any pathogens on insertion tube 252 are contained within endoscope sleeve 56 and are not allowed to escape. In this manner, endoscope 250 can then be taken to a conventional decontamination facility so that any pathogens on endoscope 250 (particularly insertion tube 252) can be removed once endoscope sleeve 56 has been removed from insertion tube 252 which is another unique aspect of the present invention.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

All of the features disclosed in this specification may be combined in any combination. Thus, unless expressly stated otherwise, each feature disclosed is only an example of a generic series of equivalent or similar features.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other modifications and implementations will occur to those skilled in the art without departing from the spirit and the scope of the invention. Accordingly, the description hereinabove is not intended to limit the invention.

Therefore, provided herein is a new and improved patient endoscopy mask, which according to various embodiments of the present invention, offers the following advantages: ease of use; lightness in weight; durability; the ability to use the mask for upper G.I. endoscopy and extubation; the use of a sleeve for covering the insertion tube of a gastroscope (upper G.I. endoscope) tube and prevent pathogens from contaminating the environment upon insertion and removal; the ability of the ET tube to provide oxygen and also function as a suction; the ability to provide negative pressure within the mask to prevent pathogens from escaping; the use of a viral filter to allow the negative pressure to draw air into the mask from the outside atmosphere without allowing pathogens to escape from the mask; the ability to use the mask in a variety of medical and non-medical settings; the use of filters to prevent the release of bacteria and viruses through patient breathing; the use of filters to further minimize the spread of infection to the healthcare providers; and the ability to provide multiple ports to connect to suction tubing and oxygen.

In fact, in many of the preferred embodiments, these advantages of ease of use, lightness in weight, durability, the ability to use the mask for upper G.I. endoscopy and extubation, the use of a sleeve for covering the insertion tube of a gastroscope and prevent pathogens from contaminating the environment upon removal, the ability of the ET tube to provide oxygen and also function as a suction, the ability to provide negative pressure within the mask to prevent pathogens from escaping, the use of a viral filter to allow the negative pressure to draw air into the mask from the outside atmosphere without allowing pathogens to escape from the mask, the ability to use the mask in a variety of medical and non-medical settings, the use of filters to prevent the release of bacteria and viruses through patient breathing, the use of filters to further minimize the spread of infection to the healthcare providers, and the ability to provide multiple ports to connect to suction tubing and oxygen are optimized to an extent that is considerably higher than heretofore achieved in prior, known patient endoscopy masks.

I claim:

1. A patient endoscopy mask, comprising:
    a mask base having an upper side and a lower side;
    an endoscope entrance port operatively connected to the upper side of the mask base;
    a sleeve assembly operatively connected to the endoscope entrance port, wherein the sleeve assembly comprises;
        an endoscope sleeve,
        a first sleeve connector operatively connected to a first end of the endoscope sleeve and operatively connected to the endoscope entrance port, and
        a second sleeve connector operatively connected to a second end of the endoscope sleeve; and
    a double clip such that the double clip is capable of being attached to the endoscopy sleeve, wherein the double clip comprises;
        a plurality of clip arms,
        a plurality of levers such that each lever is operatively connected to one of the plurality of clip arms,
        a plurality of latches such that each latch is operatively connected to one of the plurality of levers,
        a plurality of hinges such that each hinge is operatively connected to one of the plurality of plurality of clip arms, and
        a clip separator located between each of the plurality of clip arms.

2. The patient endoscopy mask, according to claim 1, wherein the patient endoscopy mask is further comprised of:
- a $CO_2$ sampling connection port operatively connected to the upper side of the mask base;
- a first oxygen ($O_2$) connection port operatively connected to the upper side of the mask base;
- a suction tip operatively connected to the upper side of the mask base;
- a suction tip sleeve located around the suction tip;
- an in-line filter suction connection port operatively connected to the upper side of the mask base;
- a second oxygen connection port operatively connected to the upper side of the mask base; and
- a viral filter operatively connected to the upper side of the mask base.

3. The patient endoscopy mask, according to claim 1, wherein the patient endoscopy mask is further comprised of:
- an endoscope having an endoscope boot and an insertion tube operatively connected to the endoscope boot, wherein the endoscope sleeve is capable of containing the insertion tube and the second sleeve connector is capable of being connected to the endoscope boot.

4. The patient endoscopy mask, according to claim 1, wherein the patient endoscopy mask is further comprised of:
- a foam cushion attached to the lower side of mask; and
- a pliable sheath located around the foam cushion.

5. The patient endoscopy mask, according to claim 4, wherein the patient endoscopy mask is further comprised of:
- a layer of an adhesive gel located adjacent to the pliable sheath; and
- an adhesive gel layer barrier located over the layer of the adhesive gel.

6. The patient endoscopy mask, according to claim 1, wherein the patient endoscopy mask is further comprised of:
- a bite block attached to the lower side of mask, wherein the bite block comprises;
  - a top part, and
  - a bottom part located adjacent to the top part.

7. A patient intubation and extubation mask, comprising:
- a mask base having an upper side and a lower side;
- an endoscope entrance port operatively connected to the upper side of the mask base;
- a sleeve assembly operatively connected to the endoscope entrance port, wherein the sleeve assembly comprises;
  - an endoscope sleeve,
  - a first sleeve connector operatively connected to a first end of the endoscope sleeve and operatively connected to the endoscope entrance port, and
  - a second sleeve connector operatively connected to a second end of the endoscope sleeve; and
- a double clip such that the double clip is capable of being attached to the endoscopy sleeve, wherein the double clip comprises:
  - a plurality of clip arms,
  - a plurality of levers such that each lever is operatively connected to one of the plurality of clip arms,
  - a plurality of latches such that each latch is operatively connected to one of the plurality of levers,
  - a plurality of hinges such that each hinge is operatively connected to one of the plurality of plurality of clip arms, and
  - a clip separator located between each of the plurality of clip arms.

8. The patient intubation and extubation mask, according to claim 7, wherein the patient intubation and extubation mask is further comprised of:
- a $CO_2$ sampling connection port operatively connected to the upper side of the mask base;
- a first oxygen ($O_2$) connection port operatively connected to the upper side of the mask base;
- a suction tip operatively connected to the upper side of the mask base;
- a suction tip sleeve located around the suction tip;
- an in-line filter suction connection port operatively connected to the upper side of the mask base;
- a second oxygen connection port operatively connected to the upper side of the mask base; and
- a viral filter operatively connected to the upper side of the mask base.

9. The patient intubation and extubation mask, according to claim 7, wherein the patient intubation and extubation mask is further comprised of:
- an endoscope having an endoscope boot and an insertion tube operatively connected to the endoscope boot, wherein the endoscope sleeve is capable of containing the insertion tube and the second sleeve connector is capable of being connected to the endoscope boot.

10. The patient intubation and extubation mask, according to claim 7, wherein the patient intubation and extubation mask is further comprised of:
- a foam cushion attached to the lower side of mask; and
- a pliable sheath located around the foam cushion.

11. The patient intubation and extubation mask, according to claim 10, wherein the patient intubation and extubation mask is further comprised of:
- a layer of an adhesive gel located adjacent to the pliable sheath; and
- an adhesive gel layer barrier located over the layer of the adhesive gel.

12. The patient intubation and extubation mask, according to claim 7, wherein the patient intubation and extubation mask is further comprised of:
- a bite block attached to the lower side of mask, wherein the bite block comprises;
  - a top part, and
  - a bottom part located adjacent to the top part.

13. A method of constructing a patient endoscopy mask, comprising:
- providing a mask base having an upper side and a lower side;
- attaching an endoscope entrance port to the upper side of the mask base;
- attaching a sleeve assembly to the endoscope entrance port, wherein the sleeve assembly comprises;
  - an endoscope sleeve,
  - a first sleeve connector operatively connected to a first end of the endoscope sleeve and operatively connected to the endoscope entrance port, and
  - a second sleeve connector operatively connected to a second end of the endoscope sleeve; and
- providing a double clip such that the double clip is capable of being attached to the endoscopy sleeve, wherein the double clip comprises:
  - a plurality of clip arms,
  - a plurality of levers such that each lever is operatively connected to one of the plurality of clip arms,
  - a plurality of latches such that each latch is operatively connected to one of the plurality of levers,
  - a plurality of hinges such that each hinge is operatively connected to one of the plurality of plurality of clip arms, and
  - a clip separator located between each of the plurality of clip arms.

14. The method of constructing a patient endoscopy mask, according to claim 13, wherein the method is further comprised of:
   attaching a $CO_2$ sampling connection port to the upper side of the mask base;
   attaching a first oxygen ($O_2$) connection port to the upper side of the mask base;
   attaching a suction tip to the upper side of the mask base;
   placing a suction tip sleeve around the suction tip;
   attaching an in-line filter suction connection port to the upper side of the mask base;
   attaching a second oxygen connection port to the upper side of the mask base; and
   attaching a viral filter to the upper side of the mask base.

15. The method of constructing a patient endoscopy mask, according to claim 13, wherein the method is further comprised of:
   providing an endoscope having an endoscope boot and an insertion tube operatively connected to the endoscope boot, wherein the endoscope sleeve is capable of containing the insertion tube and the second sleeve connector is capable of being connected to the endoscope boot.

16. The method of constructing a patient endoscopy mask, according to claim 13, wherein the method is further comprised of:
   attaching a foam cushion attached to the lower side of mask; and
   placing a pliable sheath around the foam cushion.

17. The method of constructing a patient endoscopy mask, according to claim 13, wherein the method is further comprised of:
   attaching a bite block to the lower side of mask, wherein the bite block comprises;
   a top part, and
   a bottom part located adjacent to the top part.

* * * * *